(12) United States Patent
Jee et al.

(10) Patent No.: US 10,953,054 B2
(45) Date of Patent: Mar. 23, 2021

(54) COMPOSITION COMPRISING *SARGASSUM HORNERI* EXTRACT FOR ALLEVIATING LUNG INJURY OR RESPIRATORY DISEASE

(71) Applicant: Jeju National University Industry-Academic Cooperation Foundation, Jeju-do (KR)

(72) Inventors: Young-Heun Jee, Jeju-do (KR); You-Jin Jeon, Jeju-do (KR); Hyun-Jung Kim, Jeju-do (KR); Ji-Yeon Chun, Jeju-do (KR); Areum Kim, Jeju-do (KR); Hyo-Jin Kim, Jeju-do (KR)

(73) Assignee: JEJU NATIONAL UNIVERSITY INDUSTRY-ACADEMIC COOPERATION FOUNDATION, Jeju-Do (KR)

( * ) Notice: Subject to any disclaimer, the term of this patent is extended or adjusted under 35 U.S.C. 154(b) by 93 days.

(21) Appl. No.: 16/560,007

(22) Filed: Sep. 4, 2019

(65) Prior Publication Data

US 2020/0147157 A1 May 14, 2020

(30) Foreign Application Priority Data

Nov. 13, 2018 (KR) .................. 10-2018-0139289
Nov. 13, 2018 (KR) .................. 10-2018-0139290

(51) Int. Cl.
*A61K 36/00* (2006.01)
*A61K 36/03* (2006.01)
*A61P 11/00* (2006.01)

(52) U.S. Cl.
CPC .............. *A61K 36/03* (2013.01); *A61P 11/00* (2018.01)

(58) Field of Classification Search
CPC ....................................................... A61K 36/00
USPC ......................................................... 424/725
See application file for complete search history.

(56) References Cited

FOREIGN PATENT DOCUMENTS

CN        106399120 A  *  2/2017

* cited by examiner

*Primary Examiner* — Michael V Meller
(74) *Attorney, Agent, or Firm* — Harness, Dickey & Pierce, P.L.C.

(57) ABSTRACT

Disclosed is a composition comprising a *Sargassum horneri* extract for alleviating lung injury or respiratory disease.

8 Claims, 21 Drawing Sheets

Untreated control

Dust only

Dust 125 µg/mL
+SHE 62.5 µg/mL

Dust 125 µg/mL
+SHE 125 µg/mL

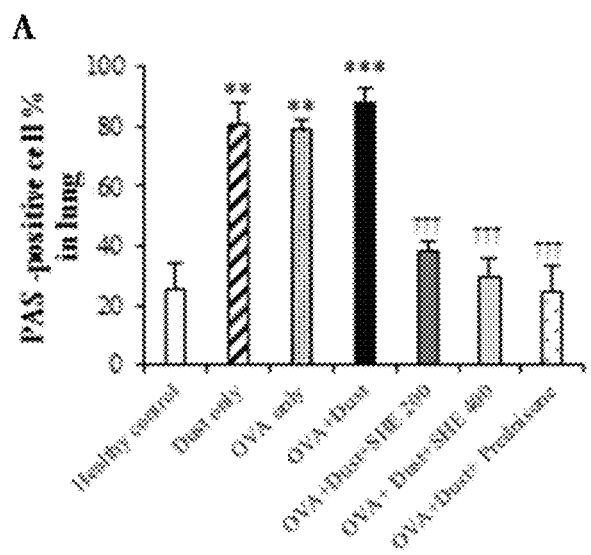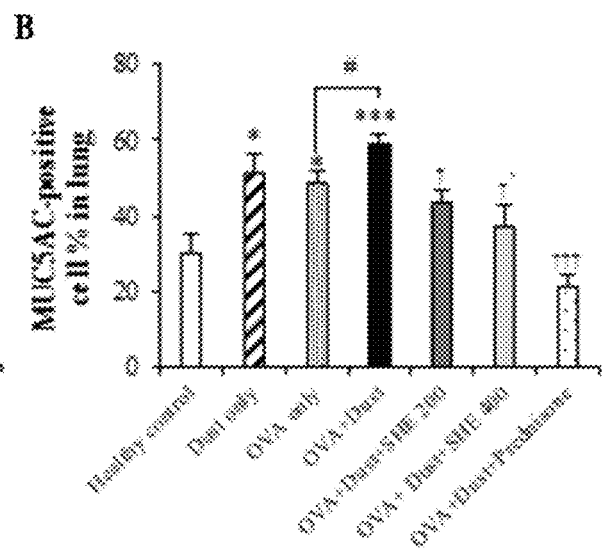
FIG. 20A
FIG. 20B

COMPOSITION COMPRISING *SARGASSUM HORNERI* EXTRACT FOR ALLEVIATING LUNG INJURY OR RESPIRATORY DISEASE

CROSS-REFERENCE TO RELATED APPLICATION

This application claims benefit of and priority to Korean Patent Application No. 10-2018-0139289 filed on Nov. 13, 2018, and Korean Patent Application No. 10-2018-0139290 filed on Nov. 13, 2018. The entire disclosure of the applications identified in this paragraph are incorporated herein by reference.

FIELD

The present disclosure relates to a composition comprising a *Sargassum horneri* extract for alleviating lung injury or respiratory disease and, more particularly to a composition for alleviating a lung injury or respiratory disease caused by particulate matter or the like.

BACKGROUND

Due to advanced industrialization, air pollution such as particulate matter (PM) has increased. In addition, desertification in the Asian continent (including China) caused by climate change has increased the occurrence of yellow dust in Korea, with the resultant increase of the public's interest in particulate matter (Kim H S, Chung Y S, Yoon M B. An analysis on the impact of large-scale transports of dust pollution on air quality in East Asia as observed in central Korea in 2014. Air Qual Atmos Health, 2015 Jan. 15 [Epub]. dx.doi.org/10.1007/s11869-014-0312-5). Particulate matter contains various components, including carbon components such as soot and organic carbons; ionic components such as chlorine, nitric acid, ammonium, sodium, and calcium; metal components such as lead, arsenic, and mercury; and polycyclic aromatic hydrocarbons such as benzopyrene (Jang An-Soo. Impact of particulate matter on health. J Korean Med Assoc, 2014; 57:763-768). In addition, primary particles from vehicle exhaust gases, quarries, construction sites and the like, and secondary particles, such as sulfates, nitrates, sulfur dioxides, nitric oxides, ammonia, volatile organic compounds and the like, produced by chemical reactions of the primary particles, contribute to particulate matter occurrence. Furthermore, particulate matter is classified according to size into two categories: a particle diameter of 2.5 to 10 μm, and a particle diameter of less than 2.5 μm. Particulate matter having a diameter of less than 2.5 μm is called fine particulate matter. Dust is caught in the nose or throat and does not affect the airway. However, if dust is smaller than 10 μm, it is deposited in the upper respiratory tract, bronchus, small airway, and alveoli, and affects the respiratory tract, causing allergic rhinitis, bronchitis, asthma, alveolar damage, etc. (Allergy Asthma Respir Dis, 2015, 3:313-319). In addition, progression to chronic inflammation can lead to chronic obstructive pulmonary disease (COPD), which causes dyspnea due to decreased pulmonary function (J Int. Korean Med, 2017, 38:353-366). It is known that particulate matter can cause not only respiratory diseases but also allergic conjunctivitis, keratitis, cardiovascular diseases, and the like, and such impacts on the human body may be caused by inflammatory reactions due to secretion of cytokines, chemokines or the like, an increase in white blood cell count, production of reactive oxygen species, etc. (Cho C C et al. In Vitro and In Vivo Experimental Studies of PM2.5 on Disease Progression, Int J Environ Res Public Health 2018, 15(7)). Accordingly, it is necessary to study substances that can inhibit such impacts.

*Sargassum horneri* is a perennial brown algae belonging to the Sargassaceae family of the Fucales order, and is known to be widely distributed in the coasts of Korea, Japan, and China and to be a major constituent of floating drifting gulfweed that travels along currents in the East Sea and the Sea of Japan (Korean J Fish Aquat Sci, 2016, 49:689-693).

It is known that *Sargassum horneri* contains various components, including fucoidan, minerals such as alginic acid, and polyphenols, and has various pharmacological and physiological functions which are helpful for beauty or health. In addition, fucoidan, a type of sulfated polysaccharide isolated from *Sargassum horneri*, has been reported to reduce oxidative stress in LPS-stimulated macrophages (Int J Biol Macromol, 2014, 68:98-106). Furthermore, it has been reported that the polyphenol component of *Sargassum horneri* has strong antioxidant activity (Journal of Medicinal Food, 2016, 19:615-628), and fucoxanthin, a type of carotenoid pigment, exhibits antioxidant, antibacterial, and anti-hypertensive effects (Mar Drugs, 2015, 13:3422-3442).

The present disclosure discloses that a *Sargassum horneri* extract has an activity of alleviating a lung injury or respiratory disease caused by particulate matter or the like.

SUMMARY

It is an object of the present disclosure to provide a composition for alleviating lung injury caused by particulate matter or the like, in which the composition contains a *Sargassum horneri* extract.

Another object of the present disclosure is to provide a composition for alleviating respiratory disease caused by particulate matter or the like, in which the composition contains a *Sargassum horneri* extract.

Other objects or specific objects of the present disclosure will be described below.

As described in Examples and Experimental Examples below, the present inventors have found that a *Sargassum horneri* extract inhibits particulate matter-induced decreases in the viability and proliferation rate of lung epithelial cells (MLE-12 cells), and in its specific mechanisms, it induces recovery from particulate matter-induced oxidative damage to lung epithelial cells, inhibits a particulate matter-induced increase in the expression of inflammatory cytokines and chemokines, inhibits the activation (i.e., phosphorylation of ERK (extracellular signal regulated kinase), p38 (MAP-kinase p38) and JNK (c-Jun N-terminal kinase), which are mechanism factors promoting the expression of these cytokines and the like. Furthermore, in a particulate matter-inhaled animal model experiment, the present inventors could confirmed that a *Sargassum horneri* extract reduced the infiltration of leukocytes, such as neutrophils, eosinophils, basophils, granulocytes, and macrophages, and inflammatory cells, such as helper T cells, cytotoxic T cells, dendritic cells, in trachea, bronchus and lung tissues; inhibited oxidative damage; reduced the infiltration of mast cells that are involved in inflammatory reactions and hypersensitive immune responses, causing bronchoconstriction, mucus secretion, etc.; and also inhibited the proliferation of goblet cells (which are mucus (phlegm) secretory cells), thus inhibiting an increase in mucus secretion.

Considering the experimental results as described above, in one aspect, the present disclosure may be directed to a composition for alleviating lung injury or improving lung function, particularly a composition for alleviating lung injury caused by particulate matter, in which the composition contains a *Sargassum horneri* extract as an active ingredient. In another aspect, the present disclosure may be directed to a composition for alleviating respiratory disease, particularly a composition for alleviating respiratory disease caused by particulate matter, in which the composition contains a *Sargassum horneri* extract as an active ingredient. In still another aspect, the present disclosure may be directed to a composition for inhibiting secretion of phlegm (mucus secreted from bronchi or lungs), in which the composition contains a *Sargassum horneri* extract as an active ingredient. In yet another aspect, the present disclosure may be directed to a composition for bronchodilation containing a *Sargassum horneri* extract as an active ingredient.

In the specification, the "*Sargassum horneri* extract" means an extract obtained by leaching the stem, leaf, whole plant or mixture thereof of the extraction target *Sargassum horneri* with water, a C1 to C4 lower alcohol (methanol, ethanol, butanol, etc.), methylene chloride, ethylene, acetone, hexane, hexane, ether, chloroform, ethyl acetate, butyl acetate, N,N-dimethylformamide (DMF), dimethylsulfoxide (DMSO), 1,3-butylene glycol, propylene glycol, or a mixed solvent thereof, which is an extract soluble in the extraction solvent; or an extract obtained using a supercritical extraction solvent, such as carbon dioxide or pentane; or a fraction obtained by fractionating the extract. As the extraction method, any method, such as cold extraction, refluxing, heating, ultrasonic irradiation, supercritical extraction, etc., may be used in consideration of the polarity of the active ingredient, the degree of extraction, and the degree of preservation. The fractionated extract is meant to include a fraction obtained by suspending the extract in a certain solvent, and then mixing the suspension with a solvent having different polarity, followed by allowing to stand, or a fraction obtained by adsorbing the crude extract onto a column packed with silica gel or the like, and then using a hydrophobic solvent, a hydrophilic solvent, or a mixed solvent thereof as a mobile phase. In addition, the meaning of the extract includes a concentrated liquid extract or solid extract obtained by removing the extraction solvent using a method such as freeze drying, vacuum drying, hot air drying or spray drying. Preferably, it means an extract obtained using water, ethanol, or a mixture thereof as an extraction solvent, more preferably an extract obtained using a mixed solvent of water and ethanol, more preferably an extract obtained using 70% ethanol, particularly a supernatant extract (an extract soluble in 95% ethanol) obtained by concentrating the extract under reduced pressure and allowing the concentrate to stand in 95% ethanol, followed by centrifugation.

In this specification, the "active ingredient" means a component that can exhibit desired activity, alone or in combination with a carrier which is not active by itself.

In this specification, "improving long function" means improving the breathing function of a non-patient (normal person), or inducing recovery from the patient's respiratory failure caused by chronic obstructive pulmonary disease, asthma, bronchitis, tracheitis or the like, or improving the breathing function of a patient.

In this specification, "alleviating lung injury" means inducing recovery from lung cell or lung tissue injury caused by particulate matter or the like or to induce recovery from lung function decline caused by lung cell or lung tissue injury.

In this specification, the "respiratory disease" is a respiratory disease caused by the mechanism of inflammatory response, hypersensitive immune response (allergic response), or both, and means asthma, chronic obstructive pulmonary disease (COPD, that is, pulmonary emphysema), tracheitis, bronchitis or rhinitis. Preferably, it means asthma, chronic obstructive pulmonary disease, or rhinitis, which is a respiratory disease in which the mechanism of particulate matter-induced inflammatory response, particulate matter-induced inflammatory hypersensitive immune response, or both is involved and which is accompanied by cough, excessive secretion of mucus (phlegm), and dyspnea. In particular, chronic obstructive pulmonary disease is caused by smoking or particulate matter, and chronic inflammation and oxidative stress are involved in the mechanism of onset thereof pathogenesis, and lung injury caused thereby is accompanied by lung function decline and the resulting dyspnea symptoms (Biol Pharm Bull, 2012, 35:1752-1760; Am J Physiol Lung CellMol Physiol, 2010, 298:L262-L269). The "respiratory disease" means chronic obstructive pulmonary disease in that the following experimental examples of the present disclosure show that a *Sargassum horneri* extract clearly alleviates particulate matter-induced inflammatory response and particulate matter-induced oxidative in lung tissue and the like.

In the composition of the present disclosure, the active ingredient may be contained in any amount (effective amount) depending on the intended use, formulation, or the like, as long as it can exhibit the effects of improving lung function, alleviating lung injury, alleviating respiratory disease, etc. The conventional effective amount thereof will be determined within a range of 0.001 wt % to 15 wt % based on the total weight of the composition. As used herein, the "effective amount" means the amount of the active ingredient contained in the composition of the present disclosure, which can exhibit intended medical/pharmacological effects, including a lung function-improving effect, a lung injury-alleviating effect, and a respiratory disease-alleviating effect, when the composition of the present disclosure is administered to a mammal, preferably a human, during the period of administration by the advice of a medical professional. This effective amount can be determined experimentally within the ordinary skill of the art.

In a specific embodiment, the composition of the present disclosure may be a food composition.

The food composition of the present disclosure may be prepared in any form. For example, it may be prepared as beverages, including teas, juices, carbonated beverages, and ionic beverages, milk, processed milk products such as yogurt, foods, including gums, rice cakes, bread, confectionery and noodles, and functional health food formulations, including tablets, capsules, pills, granules, liquids, powders, flakes, pastes, syrups, gels, jellies and bars. In addition, the food composition of the present disclosure may be legally and functionally classified as any product that complies with the regulations at the time of manufacture and distribution. For example, it may be a functional health food according to the "Korean Health Functional Foods Act", or may be confectionery, a bean product, a tea, a beverage or a special purpose food, specified on Food Codes of the "Korean Food Sanitation Act" (Food Standards and Specifications prescribed by the Minister of Food and Drug Safety).

The food composition of the present disclosure may contain food additives in addition to the active ingredient. Food additives can generally be understood as substances which are added to and mixed with or incorporated into foods during the production, processing or preservation of the foods, and their safety should be guaranteed as these additives are taken together with foods daily for a long period of time. In food additives codes according to the laws of respective countries ("Food Sanitation Act" in Korea) that regulate the production/distribution of foods, safety-guaranteed food additives are prescribed in terms of components or function. In Korean Food Additive Codes (Food Additive Standards and Specifications prescribed by the Minister of Food and Drug Safety), food additives are classified according to components into chemical synthetic products, natural additives, and mixed formulations, and these food additives are functionally classified into sweeteners, flavoring agents, preservatives, emulsifiers, acidulants, thickeners, etc.

Sweeteners are used to impart a suitable sweet taste to foods, and those of natural or synthetic origin may all be used in the composition of the present disclosure. Preferably, a natural sweetener is used, and examples of the natural sweetener include sugar sweeteners, such as corn syrup solids, honey, sucrose, fructose, lactose, and maltose.

Flavoring agents are used to improve taste and flavor, and those of natural and synthetic origin may all be used. Preferably, a natural flavoring agent is used. The use of the natural flavoring agent can be for the purpose of enhancing nutrition in addition to providing flavoring. The natural flavoring agent may be one obtained from apples, lemons, citrus fruits, grapes, strawberries, peaches, etc., or one obtained from green tea leaves, *Polygonatum odoratum*, bamboo leaves, cinnamon, *Chrysanthemum* leaves, Jasmine, etc. In addition, one obtained from ginseng (red ginseng), bamboo shoots, aloe vera, ginkgo, etc., may be used. The natural flavoring agent may be a liquid concentrate or a solid extract. In some cases, a synthetic flavoring agent may be used. As the synthetic flavoring agent, there may be used ester, alcohol, aldehyde, terpene, etc.

As a preservative, there may be used calcium sorbate, sodium sorbate, potassium sorbate, calcium benzoate, sodium benzoate, potassium benzoate, EDTA (ethylenediaminetetraacetic acid), etc. As an emulsifier, there may be used acacia gum, carboxymethyl cellulose, xanthan gum, pectin, etc., may be used. As an acidulant, there may be used formic acid, malic acid, fumaric acid, adipic acid, phosphoric acid, gluconic acid, tartaric acid, ascorbic acid, etc. The acidulant may be added to adjust the food composition to a suitable acidity for the purpose of inhibiting microbial proliferation in addition to the purpose of improving taste. As a thickener, there may be used a suspending agent, a settling agent, a gelling agent, a swelling agent, etc.

The food composition of the present disclosure may contain, in addition to the food additives as described above, physiologically active substances or minerals, which are known in the art and ensure stability as food additives, for the purpose of supplementing/enhancing functionalities and nutritional properties.

Such physiologically active substances include catechins contained in green tea and the like; vitamins such as vitamin B1, vitamin C, vitamin E, and vitamin B12; tocopherol, dibenzoyl thiamine, etc. The minerals include calcium preparations such as calcium citrate, magnesium preparations such as magnesium stearate, iron preparations such as iron citrate, chromium chloride, potassium iodide, selenium, germanium, vanadium, zinc, etc.

In the food composition of the present disclosure, the food additives as described above may be contained in appropriate amounts capable of achieving the purpose of their addition depending on the product type.

With regard to other food additives that may be contained in the food composition of the present disclosure, reference may be made to the Food Codes or Food Additive Codes according to the laws of respective countries.

In another specific embodiment, the composition of the present disclosure may be a pharmaceutical composition.

The pharmaceutical composition of the present disclosure may contain a pharmaceutically acceptable carrier in addition to the active ingredient, and may be prepared into an oral formulation or a parenteral formulation depending on the route of administration by a conventional method known in the art. As used herein, "pharmaceutically acceptable" means that the carrier does not inhibit the activity of the active ingredient and, at the same time, does not have a toxicity which is tolerable by an application (prescription) subject.

When the pharmaceutical composition of the present disclosure is prepared into an oral formulation, it may be formulated with a suitable carrier into a powder, granule, tablet, pill, sugar-coated tablet, capsule, solution, gel, syrup, suspension, wafer, or the like, according to methods known in the art. Examples of suitable pharmaceutically acceptable carriers include sugars such as lactose, glucose, sucrose, dextrose, sorbitol, mannitol, and xylitol; starches such as corn starch, potato starch and wheat starch; celluloses such as cellulose, methylcellulose, ethyl cellulose, sodium carboxymethyl cellulose, and hydroxypropylmethyl cellulose; polyvinylpyrrolidone; water, methyl hydroxybenzoate, propyl hydroxybenzoate; magnesium stearate, mineral oil, malt, gelatin, talc, polyol, vegetable oil, etc. For formulation, the composition may be formulated to contain, if necessary, diluents and/or excipients, including fillers, extenders, binders, wetting agents, disintegrants, and surfactants.

When the pharmaceutical composition of the present disclosure is prepared into a parenteral formulation, it may be formulated with a suitable carrier into an eye drop, injectable formulation, percutaneous formulation, nasal inhaler or suppository, according to methods known in the art. When the composition is formulated into an eye drop, sterile water, saline, or isotonic solution such as 5% dextrose may be used as a suitable carrier, and if necessary, benzalkonium chloride, methylparaben, ethylparaben or the like may be added for preservative purposes. When the composition is formulated as an injectable formulation, sterile water, ethanol, polyol such as glycerol or propylene glycol, or a mixture thereof, may be used as a suitable carrier, and preferably, Ringer's solution, phosphate buffered saline (PBS) containing triethanolamine, sterile water for injection, isotonic solution such as 5% dextrose, etc., may be used. When the composition is formulated into a percutaneous formulation, it may be formulated in the form of ointment, cream, lotion, gel, solution for external use, paste, liniment, aerosol or the like. For a nasal inhaler, it may be formulated in the form of an aerosol spray by using a suitable propellant such as dichlorofluoromethane, trichlorofluoromethane, dichlorotetrafluoroethane, carbon dioxide, or the like. When the composition is formulated into a suppository, witepsol, Tween 61, polyethylene glycol, cacao butter, laurin fat, polyoxyethylene sorbitan fatty ester, polyoxyethylene stearate, sorbitan fatty acid ester, etc. may be used as a base.

Specific formulation of pharmaceutical compositions is well known in the art and can be found, for example, in Remington's Pharmaceutical Sciences (19th ed., 1995), which is considered part of this specification.

The preferred dose of the pharmaceutical composition of the present disclosure is may be in the range of 0.001 mg/kg/day to 10 g/kg/day, preferably 0.001 mg/kg/day to 1 g/kg/day, depending on the patient's condition, body weight, sex, the patient's severity, and the route of administration. The administration may be carried out once or several times

BRIEF DESCRIPTION OF THE DRAWINGS

FIGS. 19A, 19B, 20A and 20B show the results of evaluating the effects of a *Sargassum horneri* extract on mucus secretion and goblet cell proliferation in the tracheas and lungs of particulate matter-inhaled animal models.

DETAILED DESCRIPTION

Figure 1A:
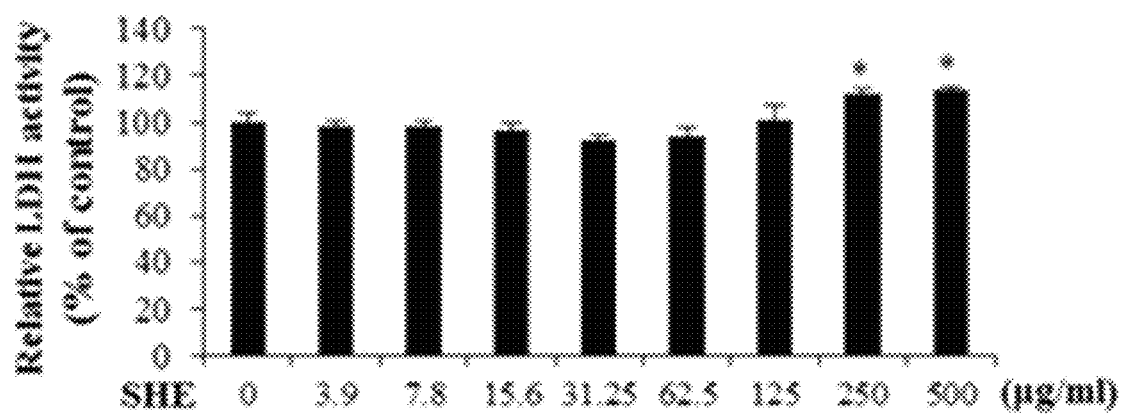
FIGS. 1A and 1B show the results of evaluating the effects of a *Sargassum horneri* extract on cytotoxicity and cell proliferation rate in lung epithelial cells.

Hereinafter, the present disclosure will be described with reference to examples and experimental examples. However, the scope of the present disclosure is not limited to these examples and experimental examples.

Example: Preparation of *Sargassum horneri* Extract

*Sargassum horneri* (whole plant) produced in Korea was washed three times with purified water for 30 minutes, and then dried to a water content of 10% or less by a hot-air dryer at 50° C. for 24 hours, and ground with a pin mill to a size of 40 to 50 mesh. 10 to 15% (w/v) of the *Sargassum horneri* powder was added to 70% alcohol and extracted using a circulation extractor at 70° C. for 12 hours, after which it was treated with white clay for food, stirred at 60 rpm for 2 hours, and centrifuged at 12,000 rpm, and the supernatant was collected. The collected supernatant was vacuum-concentrated to a volume of 1/5 using a vacuum concentrator at 60° C., and a 3-fold volume of 95% alcohol was added to the concentrate. Then, the solution was allowed to stand for 12 hours, and then the supernatant was collected by centrifugation and filtration. The collected extract was concentrated to a volume of 1/5 using a vacuum concentrator, and then dried with a freeze dryer, thereby obtaining a *Sargassum horneri* ethanol extract powder (SHE).

EXPERIMENTAL EXAMPLES: EXPERIMENTS ON RESPIRATORY DISEASE-ALLEVIATING ACTIVITY OF *SARGASSUM HORNERI* EXTRACT

Experimental Example 1: Effects of *Sargassum horneri* Extract on Cytotoxicity and Cell Proliferation Rate in Lung Epithelial Cells (1) Lactose dehydrogenase (LDH), a cytosolic enzyme, is released extracellularly when the cell membrane is damaged. LDH catalyzes the dehydrogenation of lactic acid to produce pyruvate and NADH, and the NADH reduces tetrazolium salt (INT) to red formazan by the catalytic action of diaphorase (Part Fibre Toxicol 2017, 14:39). The activity of LDH was measured to evaluate the effect of the SHE on murine lung epithelial cell line 12 (hereinafter referred to as MLE-12). In addition, using the amount of LDH released, $IC_{50}$ (at which 50% of cells lose their viability by the SHE) was calculated. In addition, the extent of incorporation of $^3H$-thymidine was evaluated to evaluate cell proliferation rate.

(2) MLE-12 Cells

MLE-12 cells were added to Ham's F12 medium (supplemented with 0.05 mg/ml of insulin, 0.01 mg/ml of transferrin, 30 nM sodium selenite, 10 nM hydrocortisone, 10 nM β-estradiol, 10 mM HEPES, 2 mM L-glutamine, and 2% fetal bovine serum), and dispensed in a 96-well plate at a density of $1\times10^3$ cells/well. The cells were incubated in a 5% $CO_2$ incubator at 37° C. for 12 hours, and then treated with various concentrations (0 to 500 μg/ml) of the SHE, and incubated for 48 hours. Then, the cytotoxicity was analyzed using a LDH Cytotoxicity Detection Kit (Takara Bio Inc., Japan), and the $IC_{50}$ (half maximal inhibitory concentration) was analyzed using the SigmaPlot V10.0 (Systat Software, Inc., Richmond, Calif., USA) program. Meanwhile, MLE-12 cells were dispensed in a 96 well plate at a density of $2 \times 10^4$ cells/well, and incubated in a 5% $CO_2$ incubator at 37° C. for 12 hours, after which the cells were treated with various concentrations (0 to 500 µg/ml) of the SHE, and incubated in a 5% $CO_2$ incubator at 37° C. for 54 hours. Next, each well was treated with 1 µCi of $^3$H-thymidine (42 Ci/nmol, Amersham Life Science, Arling-ton Heights, Ill., USA), and incubated in a 5% $CO_2$ incubator at 37° C. for 18 hours, after which the cells were captured on a glass fiber filter, and the amount of radioisotopes therein was measured using a radioactivity meter (Wallac MicroBeta® TriLux, Perkin Elmer, Waltham, Mass., USA).

Figure 1B:
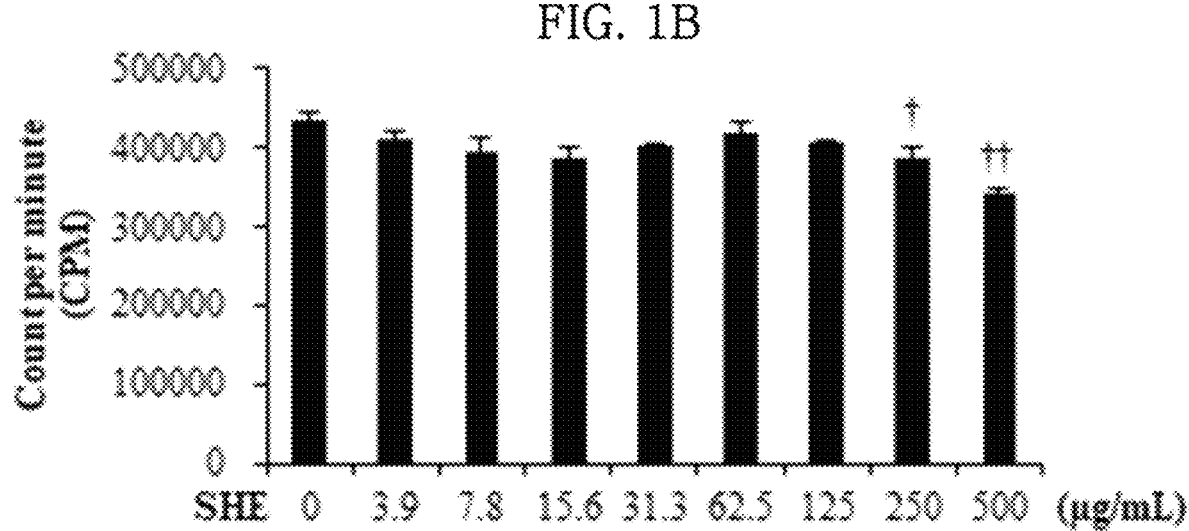

(3) The results are shown in FIG. 1. When the MLE-12 cells were treated with various concentrations (0 to 500 µg/ml) of the SHE, SHE-induced cytotoxicity did not appear at a concentration of 0 to 125 µg/ml (FIG. 1A). However, treatment with a high concentration (250 or 500 µg/ml) of the SHE showed cytotoxicity (FIG. 1A). In addition, treatment with 0 to 125 µg/ml of the SHE had no effect on the cell proliferation rate, but treatment with 250 and 500 µg/ml of the SHE reduced the cell proliferation rate by 11.0% and 21.2%, respectively (FIG. 1B).

Experimental Example 2: Effects of *Sargassum horneri* Extract (SHE) on Cytotoxicity and Proliferation Rate in MLE-12 Cells Damaged by Particulate Matter (1) Lactose dehydrogenase (LDH), a cytosolic enzyme, is released extracellularly when the cell membrane is damaged. LDH catalyzes the dehydrogenation of lactic acid to produce pyruvate and NADH, and the NADH reduces tetrazolium salt (INT) to red formazan by the catalytic action of diaphorase. The activity of LDH was measured to determine the degree of particulate matter-induced cell damage in MLE-12 cells and to evaluate the effect of the SHE on protection from cell damage. In addition, using the amount of LDH released, $IC_{50}$ (at which 50% of cells lose their viability by particulate matter and the SHE) was calculated. In addition, the extent of incorporation of $^3$H-thymidine was evaluated to evaluate cell proliferation rate. In addition, the extent of incorporation of $^3$H-thymidine was evaluated to evaluate cell proliferation rate.

(2) MLE-12 cells were added to Ham's F12 medium (supplemented with 0.05 mg/ml of insulin, 0.01 mg/ml of transferrin, 30 nM sodium selenite, 10 nM hydrocortisone, 10 nM β-estradiol, 10 mM HEPES, 2 mM L-glutamine, and 2% fetal bovine serum), and dispensed in a 96-well plate at a density of $1 \times 10^3$ cells/well. The cells were incubated in a 5% $CO_2$ incubator at 37° C. for 12 hours, and then treated with various concentrations (31.3 and 125 500 µg/ml) of the SHE and various concentrations (3.9 to 250 µg/ml) of particulate matter, and incubated for 48 hours. Then, the cytotoxicity was analyzed using a LDH Cytotoxicity Detection Kit (Takara Bio Inc., Japan), and the $IC_{50}$ was analyzed using the SigmaPlot V10.0 (Systat Software, Inc., Richmond, Calif., USA) program. Meanwhile, MLE-12 cells were dispensed in a 96 well plate at a density of $2 \times 10^4$ cells/well, and incubated in a 5% $CO_2$ incubator at 37° C. for 12 hours, after which the cells were treated with various concentrations (31.3 and 125 µg/ml) of the SHE and various concentrations (3.9 to 250 µg/ml) of particulate matter, and incubated in a 5% $CO_2$ incubator at 37° C. for 54 hours. Next, each well was treated with 1 µCi of $^3$H-thymidine (42 Ci/nmol, Amersham Life Science, Arling-ton Heights, Ill., USA), and incubated in a 5% $CO_2$ incubator at 37° C. for 18 hours, after which the cells were captured on a glass fiber filter, and the amount of radioisotopes therein was measured using a radioactivity meter (Wallac MicroBeta® TriLux, Perkin Elmer, Waltham, Mass., USA).

Figure 2A:
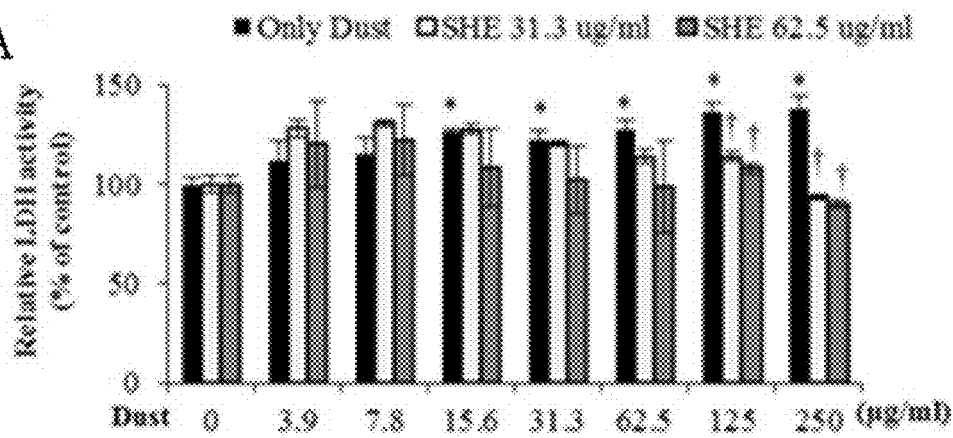
FIGS. 2A, 2B, and 2C show the results of evaluating the effects of a *Sargassum horneri* extract on cytotoxicity and cell proliferation rate in lung epithelial cells damaged by particulate matter.
Figure 2B:
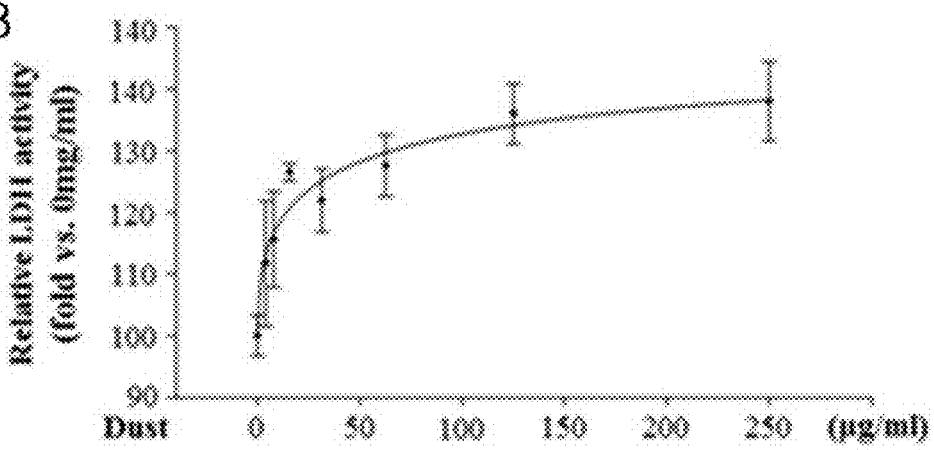
Figure 2C:
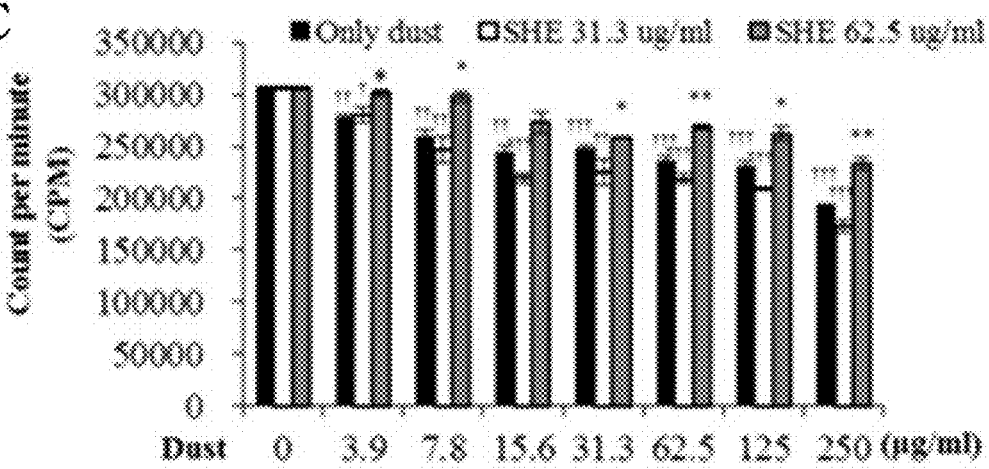

(3) The results are shown in FIG. 2. When the MLE-12 cells were treated with various concentrations (0 to 250 µg/ml) of particulate matter, the particulate matter showed concentration-dependent cytotoxicity from a concentration of 15.6 µg/ml (FIG. 2A), and at a particulate matter treatment concentration of 44.15 µg/ml, 50% of the MLE-12 cells lost their viability ($IC_{50}$=44.15 µg/ml) (FIG. 2B). However, when the cells were treated with particulate matter and 31.3 and 62.5 µg/ml of the SHE, the high-concentration particulate matter-treated group (125 or 250 µg/ml) which has shown cytotoxicity showed a concentration-dependent decrease in cytotoxicity (P; *<0.05, †<0.05) (FIG. 2A). In addition, as the particulate matter treatment concentration (0 to 250 µg/ml) increased, the cell proliferation rate significantly decreased (P; *<0.05, †<0.05). However, when the cells were treated with the SHE and 3.9 to 250 µg/ml of particulate matter, the cell proliferation rate significantly increased (P; *<0.05, **<0.005, †<0.05) (FIG. 2C).

Experimental Example 3: Effect of *Sargassum horneri* Extract (SHE) on Oxidative Stress in MLE-12 Cells Damaged by Particulate Matter (1) Reactive oxygen species (ROS) convert non-fluorescent DCF-DA to the fluorescent substance DCF by oxidation. In order to evaluate the antioxidant effect of the *Sargassum horneri* extract (SHE) on MLE-12 cells damaged by particulate matter, the fluorescence intensity of DCF was measured.

(2) MLE-12 cells were dispensed in a 24-well plate at a density of $1.5 \times 10^5$ cells/well and incubated for 12 hours. Then, the cells were treated with the SHE (62.5, 125 and 250 µg/ml) and particulate matter (62.5 and 125 µg/ml) and incubated in a 5% $CO_2$ incubator at 37° C. for 48 hours. Next, the cells were harvested, washed with Dulbecco's phosphate-buffered saline (DPBS), and then treated with 25 µM DCF-DA and incubated in a 5% $CO_2$ incubator at 37° C. for 30 minutes, after which the fluorescence intensity of DCF was measured using a CytoFLEX flow cytometer (Beckman coulter, Inc., Brea, Calif., USA).

Figure 3:
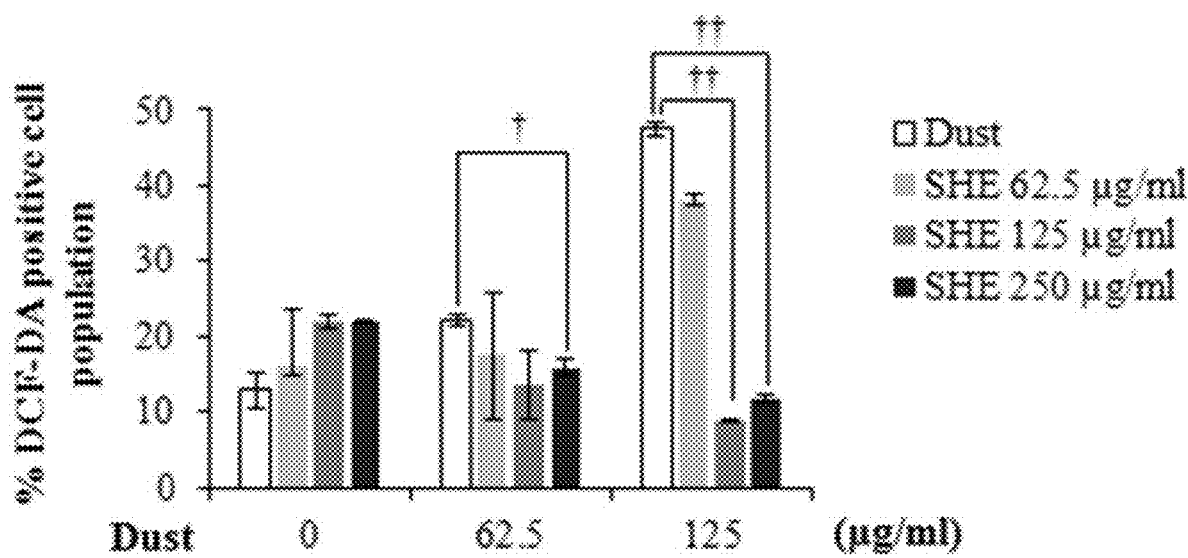
FIG. 3 shows the results of evaluating the effect of a *Sargassum horneri* extract on oxidative stress in lung epithelial cells damaged by particulate matter.

(3) The results are shown in FIG. 3. When the MLE-12 cells were treated with various concentrations (62.5 and 125 µg/ml) of particulate matter showing cytotoxicity, the particulate matter increased ROS production in a concentration-dependent manner, and when the cells were treated with particulate matter and various concentrations (62.5, 125, and 250 µg/ml) of the SHE, ROS production showed a tendency to decrease. In particular, when the cells were treated with 125 µg/ml of particulate matter and 125 and 250 µg/ml of the SHE, ROS production decreased by 5.3-fold and 4.0-fold, respectively (FIGS. 3A and 3B).

Experimental Example 4: Effect of *Sargassum horneri* Extract (SHE) on Lipid Peroxidation in MLE-12 Cells Damaged by Particulate Matter (1) The content of malondialdehyde (hereinafter referred to as MDA), a measure of lipid peroxidation, was measured to evaluate the lipid peroxidation inhibitory effect of the *Sargassum horneri* extract (SHE) in MLE-12 cells damaged by particulate matter.

(2) MLE-12 cells were dispensed in a 10-cm dish at a density of $1 \times 10^6$ cells, and then incubated in a 5% $CO_2$ incubator at 37° C. for 12 hours to induce cell adhesion. Then, the cells were treated with SHE (62.5 and 125 μg/ml) and particulate matter (62.5 and 125 μg/ml) and incubated in in a 5% $CO_2$ incubator at 37° C. for 6, 24 and 48 hours. Next, the cells were harvested, washed cold DPBS, and added to the NE-PER® Nuclear and Cytoplasmic extraction kit (Thermo scientific, Rockford, USA), and protease inhibitors (2 mM $Na_3VO_4$, 1 mM PMSF, 10 μg/ml aprotinin, and 10 μg/ml leupeptin) were added to the kit to extract protein. 10% (w/v) trichloroacetic acid was added to the extracted protein and allowed to react on ice for 10 minutes, and then the supernatant was separated by centrifugation at 2000 g and 4° C. for 15 minutes. The same amount of 0.67% (w/v) thiobarbituric acid (TBA, 0.67% (w/v) solution in 50 mM TBA) was added to the supernatant and heated at 100° C. for 10 minutes, followed by centrifugation at 1000 g and 4° C. for 10 minutes. Then, the absorbance of the supernatant at 532 nm was measured using an ELISA plate reader.

Figure 4:
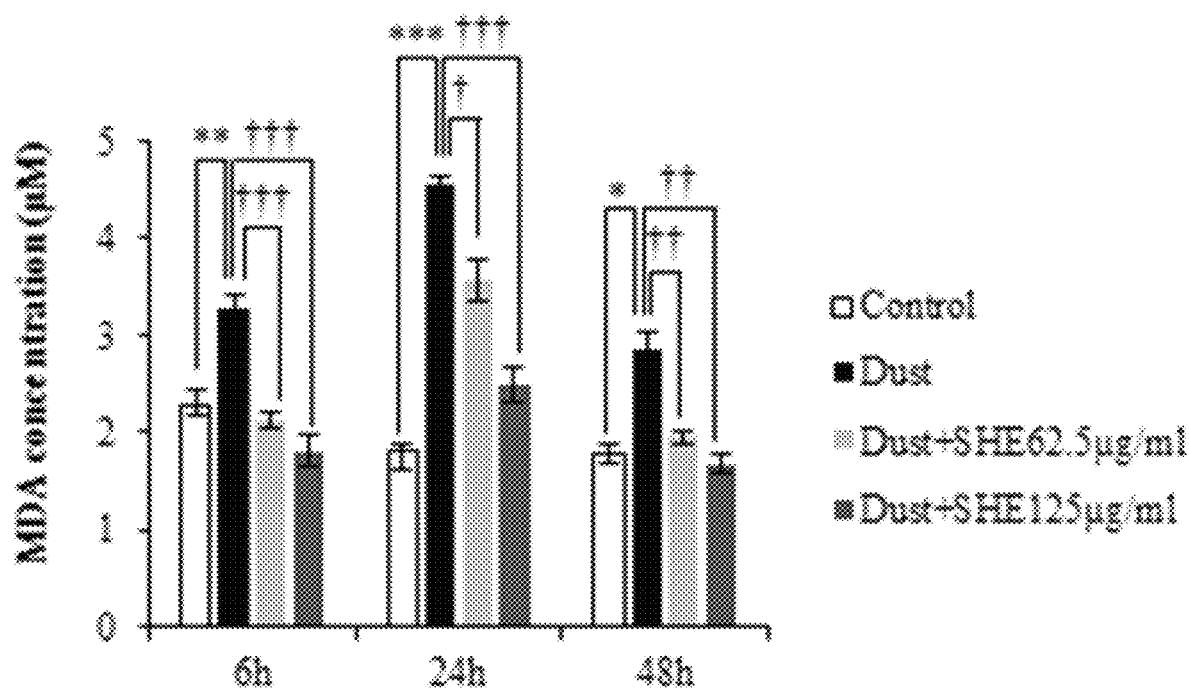
FIG. 4 shows the results of evaluating the effect of a *Sargassum horneri* extract on lipid peroxidation in lung epithelial cells damaged by particulate matter.
Figure 5A:
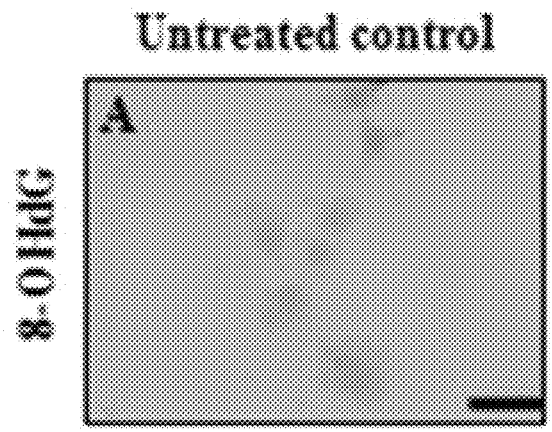
FIGS. 5A, 5B, 5C and 5D show the results of evaluating the effect of a *Sargassum horneri* extract on oxidative stress-induced DNA damage in lung epithelial cells damaged by particulate matter.
Figure 5B:
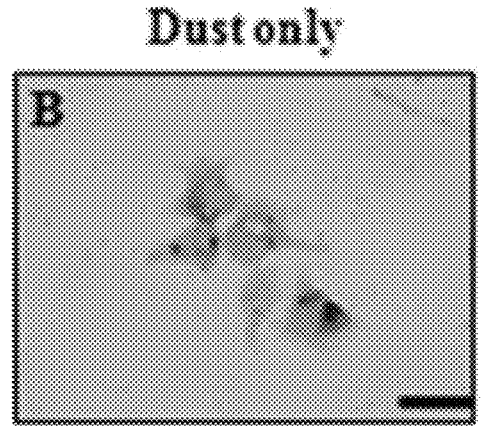
Figure 5C:
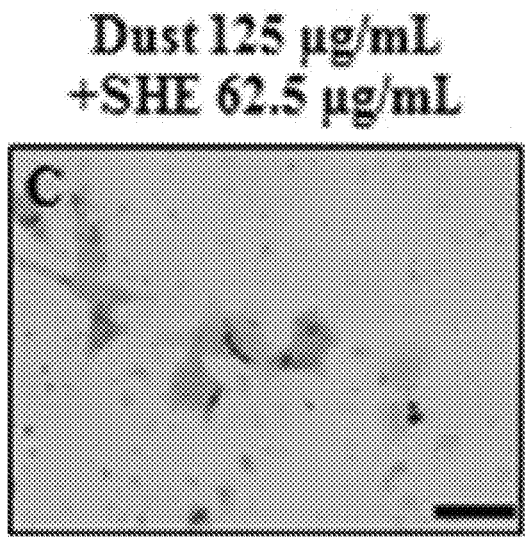
Figure 5D:
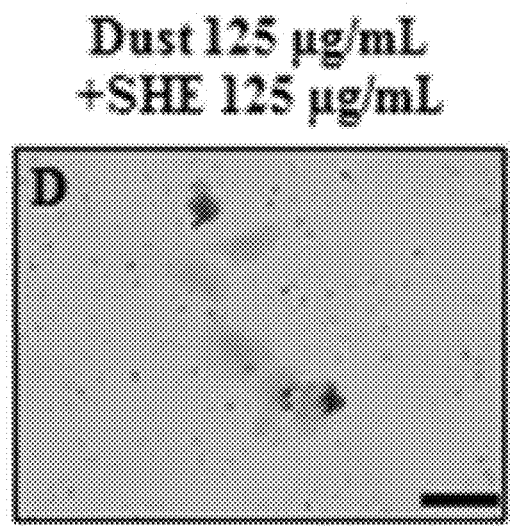
Figure 6A:
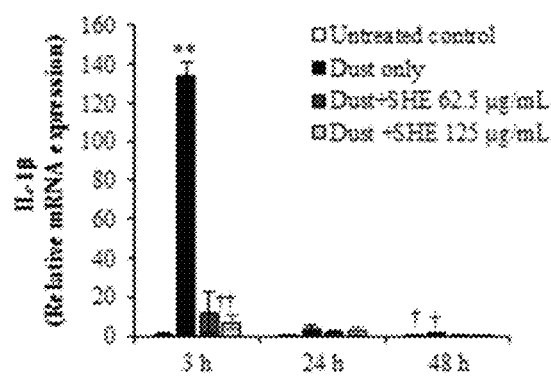
FIGS. 6A, 6B, 6C, 6D, 7A, 7B and 7C show the results of evaluating the effects of a *Sargassum horneri* extract on the expression of inflammatory cytokines and chemokines and inflammatory mediators in lung epithelial cells damaged by particulate matter.
Figure 6B:
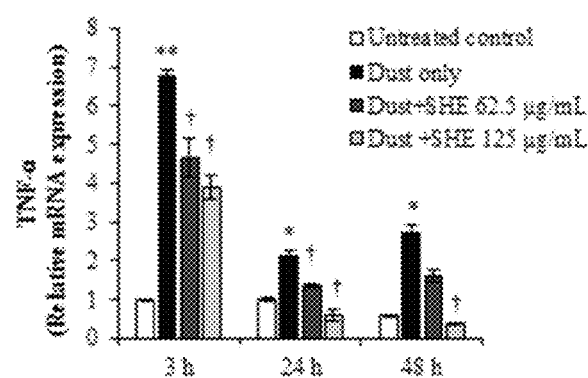
Figure 6C:
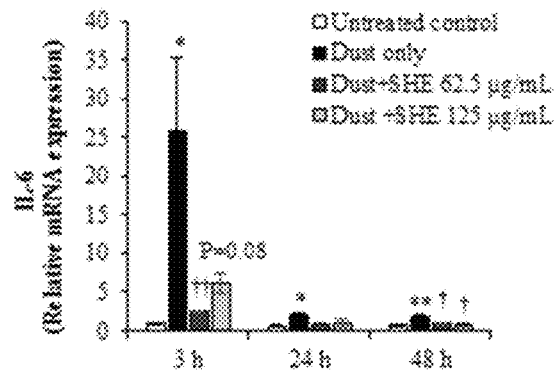
Figure 6D:
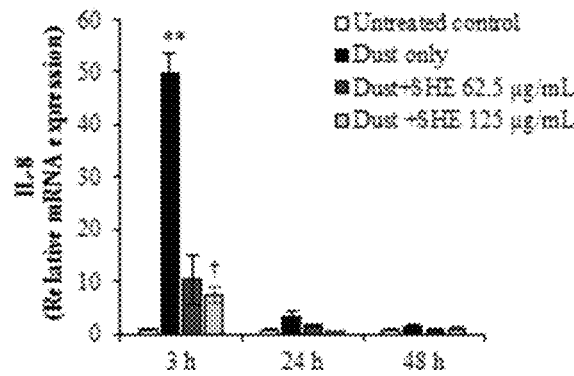

(3) The results are shown in FIG. 4. When the MLE-12 cells were incubated with 125 μg/ml of particulate matter for 6, 24 and 48 hours, the content of MDA significantly increased. In particular, when the cells were incubated for 24 hours, the content of MDA increased by 2.5-fold compared to the control group not treated with particulate matter. In addition, when the cells were treated with particulate matter and various concentrations (62.5 and 125 μg/ml) of the SHE, the content of MDA significantly decreased in a concentration-dependent manner at 6, 24 and 48 hours (FIG. 4).

Experimental Example 5: Effect of *Sargassum horneri* Extract (SHE) on Oxidative Stress-Induced DNA Damage in MLE-12 Cells Damaged by Particulate Matter (1) 8-Hydroxy-2'-deoxyguanosine (8-OHdG), a marker of oxidative stress-induced DNA damage, is produced when the hydroxyl group at position 8 of a guanine molecule among DNA bases is oxidized (Particle and fibre toxicology, 2017, 14(38)). 8-OHdG is used as a marker for evaluating the degree of DNA damage caused by reactive oxygen species (ROS) that causes oxidative stress. Thus, MLE-12 cells were treated with particulate matter, and the degree of DNA damage caused by particulate matter and the DNA damage inhibitory effect of the *Sargassum horneri* extract (SHE) were evaluated by immunocytochemistry (ICC).

(2) MLE-12 cells were dispensed in 12-well plates containing a coated coverslip at a density of $8 \times 10^4$ cells per well, and then incubated in a 5% $CO_2$ incubator at 37° C. for 12 hours to induce cell adhesion. Next, the cells were treated with the SHE (62.5 and 125 μg/ml) and particulate matter (125 μg/ml) and incubated in a 5% $CO_2$ incubator at 37° C. for 24 hours. Then, the cells were washed, fixed in 4% paraformaldehyde (in PBS, pH 7.4), and then washed and subjected to immunocytochemistry (ICC). To analyze the expression of 8-OHdG in the MLE-12 cells, the cells were allowed to react with an anti-8-OHdG antibody (1:1000) at room temperature for 1 hour. After completion of the reaction, the cells were allowed to react with biotinylated anti-goat IgG at room temperature for 30 minutes and developed with 3,3'-diaminobenzidine (DAB), and positive cells were counterstained with a hematoxylin solution, and then observed with an optical microscope.

The results of observation with the optical microscope are shown in FIG. 5. The results of analyzing the expression of 8-OHdG indicated that the expression of 8-OHdG in the MLE-12 cells increased in the group treated with particulate matter alone (Dust only group) compared to the untreated control group (FIGS. 5A and 5B). It was observed that when the cells were treated with particulate matter and the SHE, the expression of 8-OHdG decreased in the group treated with the SHE compared to the group treated with particulate matter alone (Dust only group), and the expression of 8-OHdG effectively decreased as the concentration of the SHE increased (FIGS. 5C and 5D).

Experimental Example 6: Effect of *Sargassum horneri* Extract (SHE) on Expression of Cytokines and Chemokines in MLE-12 Cells Damaged by Particulate Matter (1) Using quantitative reverse transcription real-time PCR (qRT-PCR), the mRNA expression levels of inflammatory cytokines (IL-1β, TNF-α, IL-6, and IL-8) and chemokines (MCP1, and CCL5) were measured to evaluate the anti-inflammatory effect of the *Sargassum horneri* extract (SHE) on the MLE-12 cells damaged by particulate matter.

(2) MLE-12 cells were dispensed in a 10-cm dish at a density of $5 \times 10^6$ cells, and then incubated in a 5% $CO_2$ incubator at 37° C. for 12 hours to induce cell adhesion. Next, the cells were treated with the SHE (62.5 and 125 μg/ml) and particulate matter (125 μg/ml) and incubated in a 5% $CO_2$ incubator at 37° C. for 3, 24 and 48 hours. Thereafter, the cells were harvested and washed with DPBS, and RNA was extracted using Trizol reagent (Life technologies). Then, 500 μl of chloroform (Sigma-Aldrich) was added to and mixed well with the RNA and centrifuged at 15,000 g for 15 minutes, and the supernatant was collected and isopropanol was added thereto, followed by centrifugation at 12,000 g and 4° C. for 10 minutes. After centrifugation, the RNA pellet was washed with 70% EtOH, dried at room temperature, and synthesized into cDNA using the Promega A3500 cDNA synthesis kit (St Louis, Cam USA). The cDNA was subjected to PCR using the StepOnePlus real-time PCR system (Applied Biosystems, Foster City, Calif.) and the Power SYBR Green PCR Master Mix (Applied Biosystems, USA). The primers used in this experiment were as follows: IL-1β: 5'-GCT ACC TGT GTC TTT CCC GTC G-3', 5'-TTG TCG TTG CTT GGT TCT CCT TG-3'; TNF-α: 5'-GGC AGC TTC TGT CCC TTT CAC TC-3', 5'-CAC TTG GTG GTT TGC TAC GAC G-3'; MCP1: 5-AACTGAAGCTCGCACTCTCG-3', 5'-TCAGCACAGATCTCCTTGGC-3'; CCL5: 5'-GGAGT-ATTTCTACACCAGCAGCAAG-3', 5'-GGCTAGGACTAGAGCAAGCAATGAC-3'; COX2: 5'-GCA AAT CCT TGC TGT TCC AAT C-3', 5'-GGA GAA GGC TTC CCA GCT TTT G-3'; GAPDH: 5'-AAC GAC CCC TTC ATT GAC C-3', 5'-TCA GAT GCC TGC TTC ACC C-3'.

Figure 7A:
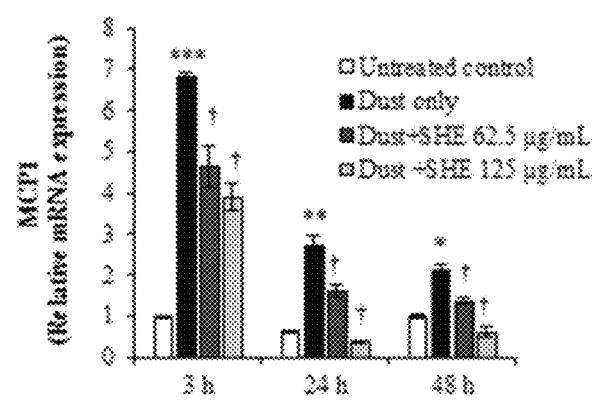
Figure 7B:
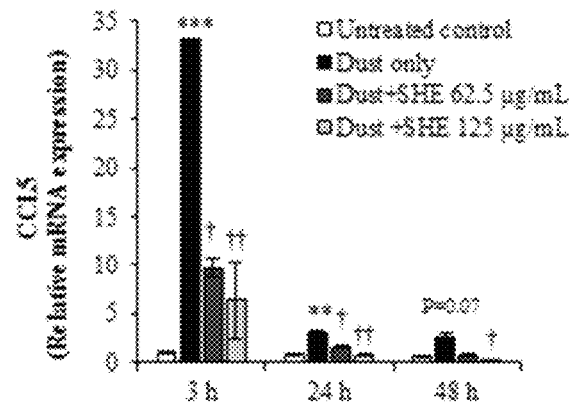
Figure 7C:
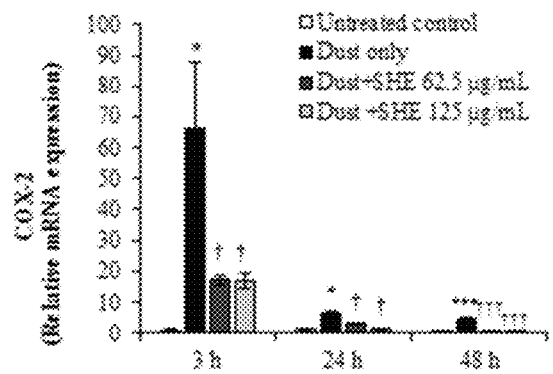
Figure 8A:
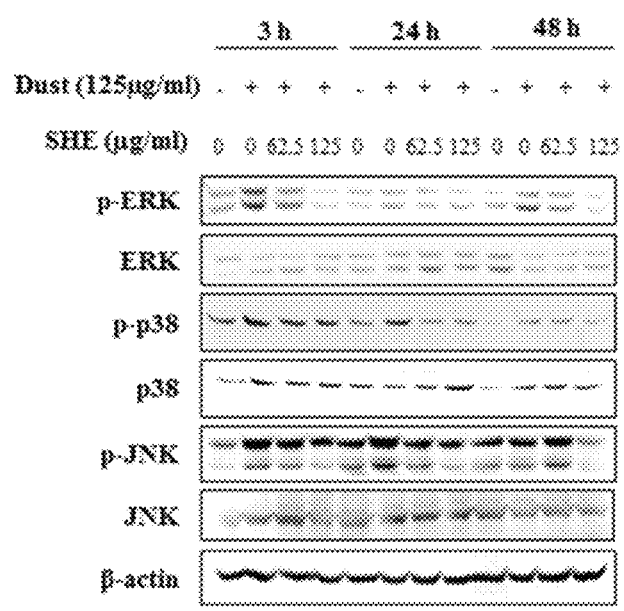
FIGS. 8A, 8B, 8C and 8D show the results of evaluating the effects of a *Sargassum horneri* extract on the mechanism of secretion of inflammatory cytokines in lung epithelial cells damaged by particulate matter.
Figure 8B:
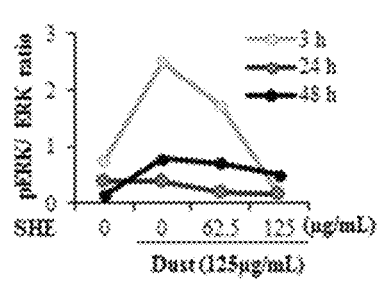
Figure 8C:
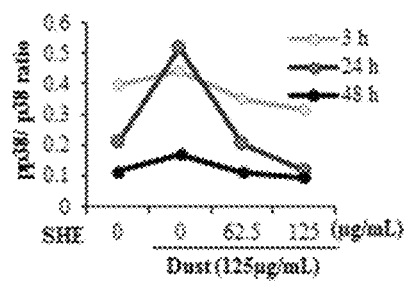
Figure 8D:
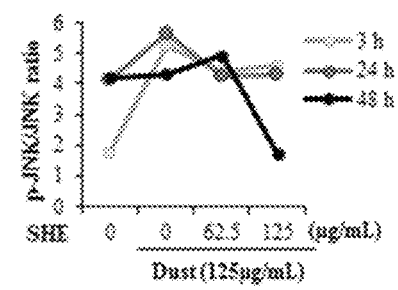

(3) The results are shown in FIGS. 6 and 7. When the MLE-12 cells were treated with 125 μg/ml of particulate matter and incubated for 3, 24 and 48 hours, the mRNA expression expressions of IL-1β, TNF-α, IL-6, IL-8, MCP1, CCL5 and COX-2 all increased compared to those in the group not treated with particulate matter. When the cells were treated with particulate matter and 62.5 and 125 μg/ml of the SHE, the mRNA expression expressions of IL-1β, TNF-α, IL-6, IL-8, MCP1, CCL5 and COX-2 significantly decreased.

Experimental Example 7: Effect of *Sargassum horneri* Extract (SHE) on the Mechanism of Secretion of Inflammatory Cytokines in MLE-12 Cells Damaged by Particulate Matter (1) The expression levels of MAP-kinase p38, c-Jun N-terminal kinase (JNK) and extracellular signal regulated kinase (ERK) in a mitogen-activated protein kinase (MAPK) pathway, which is a cell signaling mechanism involved in various intracellular mechanisms, including cell growth, cell differentiation and cell death, were measured to evaluate the effect of the *Sargassum horneri* extract (SHE) on the MAPK signaling pathway in MLE-12 cells damaged by particulate matter.

(2) MLE-12 cells were dispensed in a 10-cm dish at a density of $1\times10^7$ cell, and then incubated in a 5% $CO_2$ incubator at 37° C. for 12 hours to induce cell adhesion. Next, the cells were treated with SHE (62.5 and 125 μg/ml) and particulate matter (125 μg/ml) and incubated in a 5% $CO_2$ incubator at 37° C. for 3, 24 and 48 hours. The cytosolic protein in the MLE-12 cells was isolated using the NE-PER® Nuclear and Cytoplasmic extraction kit (Thermo scientific, Rockford, USA). 40 μg of the cytosolic protein was electrophoresed on SDS-PAGE (10-12%), and the separated protein was transferred to a nitrocellulose membrane at 100V for 120 minutes. Next, to inhibit non-specific reactions, the membrane was allowed to react with 2% skim milk (Maeil, South of Korea) at room temperature for 1 hour, and allowed to react with p-38 (1:1000, Cell signaling Technology, MA, USA), phospho-p38 (1:1000, Cell signaling Technology, MA, USA), ERK (1:1000, Cell signaling Technology, MA, USA), phospho-ERK (1:1000, Cell signaling Technology, MA, USA), JNK (1:200, Santa Cruz Biotechnology, CA, USA), and p-JNK (1:200, Santa Cruz Biotechnology, CA, USA) antibodies for hour, and then allowed to react at 4° C. overnight. Next, the membrane was allowed to react with horseradish peroxidase (HRP)-conjugated anti-mouse IgG, anti-rabbit IgG (1:2000, Invitrogen, Carlsbad, Calif., USA) for 45 minutes. Color development was performed using Westzol (tNtRON Biotechnology, Sungnam, Korea), and band images were obtained using Fusion Solo® (Vilber Lourmat, Eberhardzell, Germany). The band images were analyzed using the Image J software (v1.46), and intensity was calculated by comparing the expression level with β-actin (1:2000, Sigma, Saint Louis, USA).

(3) The results are shown in FIG. 8. When the MLE-12 cells were treated with 125 μg/ml of particulate matter and incubated for 3 hours, the phosphorylation of ERK, p38 and JNK increased. When the MLE-12 cells were treated with 125 μg/ml of particulate matter and incubated for 3 hours, the phosphorylation of ERK increased by 3.4-fold compared to that in the untreated group, and when the cells were treated with particulate matter and 62.5 μg/ml of the SHE, the phosphorylation of ERK decreased by 2.0-fold, and when the cells were treated with particulate matter and 125 μg/ml of the SHE, the phosphorylation of ERK decreased by 14.0-fold (FIGS. 8A and 8B). When the MLE-12 cells treated with 125 μg/ml of particulate matter and incubated for 3 hours, the phosphorylation of p38 increased by 1.1-fold compared to that in the untreated group, and when the cells were treated with particulate matter and 62.5 μg/ml of the SHE, the phosphorylation of p38 decreased by 1.3-fold, and when the cells were treated with particulate matter and 125 μg/ml of the SHE, the phosphorylation of p38 decreased by 1.4-fold (FIGS. 8A and 8C). When the MLE-12 cells treated with 125 μg/ml of particulate matter and incubated for 24 hours, the phosphorylation of p38 increased by 2.4-fold compared to that in the untreated group, and when the cells were treated with particulate matter and 62.5 μg/ml of the SHE, the phosphorylation of p38 decreased by 2.5-fold, and when the cells were treated with particulate matter and 125 μg/ml of the SHE, the phosphorylation of p38 decreased by 4.6-fold (FIGS. 8A and 8C). When the MLE-12 cells were treated with 125 μg/ml of particulate matter and incubated for 3 hours, the phosphorylation of JNK increased by 3.0-fold compared to that in the untreated group, and when the cells were treated with particulate matter and 62.5 μg/ml of the SHE, the phosphorylation of JNK decreased by 1.2-fold, and when the cells were treated with particulate matter and 125 μg/ml of the SHE, the phosphorylation of JNK decreased by 1.1-fold (FIGS. 8A and 8D). In addition, when the MLE-12 cells were treated with 125 μg/ml of particulate matter and incubated for 24 hours, the phosphorylation of JNK increased by 1.4-fold compared to that in the untreated group, and when the cells were treated with particulate matter and 62.5 μg/ml of the SHE, the phosphorylation of JNK decreased by 1.3-fold, and when the cells were treated with particulate matter and 125 μg/ml of the SHE, the phosphorylation of JNK decreased by 1.4-fold (FIGS. 8A and 8D).

Experimental Example 8: Experimental Animal Models

Figure 9:
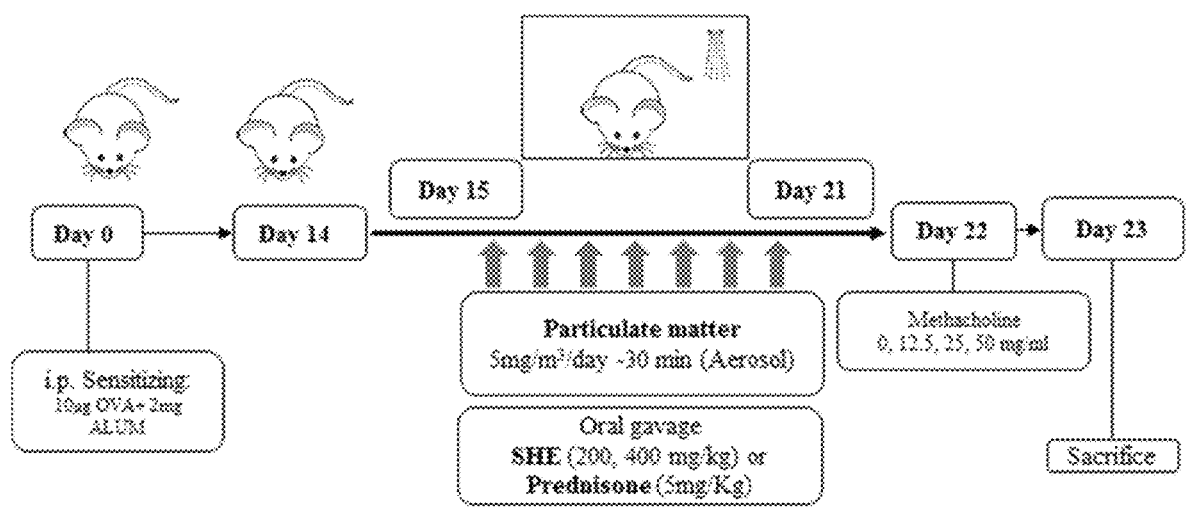
FIG. 9 schematically shows the construction of test groups in experimental animal models, the time of sample administration, the period of sample administration, etc.

Experimental Example 8-1: Construction of Experimental Groups and Administration of Sample As experimental animals, four 7-8-week-old BALB/c mice per group were used. The experimental groups used were divided into a normal control group (hereinafter referred to as healthy control group), a group inhaled with particulate matter alone (hereinafter referred to as dust only group), an ovalbumin (hereinafter referred to as OVA)-sensitized group (hereinafter OVA only), an OVA sensitized+particulate matter-inhaled group (hereinafter referred to as OVA+dust group), an OVA sensitized+particulate matter-inhaled and sample-administered group (hereinafter referred to as OVA+dust+200 mg/kg SHE group or OVA+dust+400 mg/kg SHE group), and an OVA-sensitized+particulate matter-inhaled and allergic respiratory inflammation anti-inflammatory drug (Prednisone)-administered group (OVA+dust+5 mg/kg Prednisone group). 10 μg of OVA and 2 mg of $Al(OH)_3$ were mixed well with 200 μl of saline, and then intraperitoneally (i.p.) administered once to BALB/c mice. After 15 days, particulate matter was inhaled daily into the particulate matter-inhaled group at a concentration of 5 mg/m³ by nebulizer for 30 minutes during a period of 7 days. Together with inhalation of particulate matter, 200 or 400 mg/kg of the SHE was orally administered daily to the SHE-administered group, and 5 mg/kg of prednisone was orally administered daily to the allergic respiratory inflammation-treated group (FIG. 9).

Experimental Example 8-2: Effect of *Sargassum horneri* Extract (SHE) on Differential Cell Count in Blood of Particulate Matter-Inhaled Animal Models (1) The BALB/c mice were euthanized, and then blood was sampled by cardiac puncture using a heparin syringe, thereby obtaining mouse blood for each group. Then, the blood was plated on a slide glass to a thin thickness, and then stained with Diff Quick solution, and neutrophils, lymphocytes, monocytes, eosinophils, and basophils were counted under a microscope and compared.

Figure 10A:
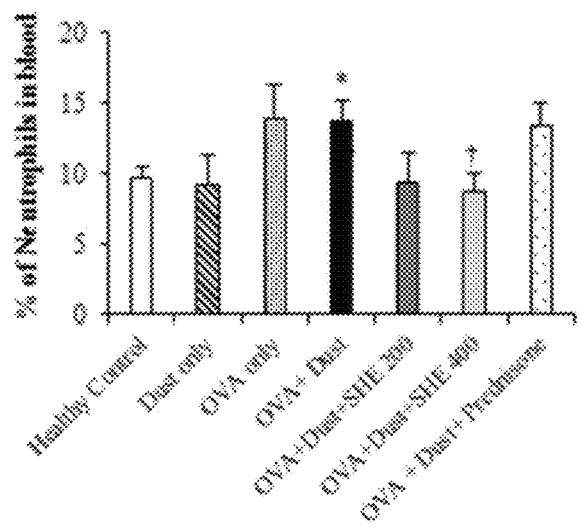
FIGS. 10A, 10B, 10C, 11A and 11B show the results of evaluating the effect of a *Sargassum horneri* extract on differential cell count in the blood of particulate matter-inhaled animal models.
Figure 10B:
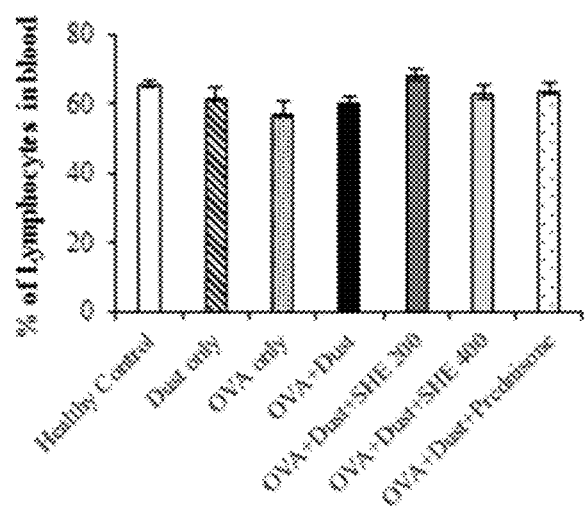
Figure 10C:
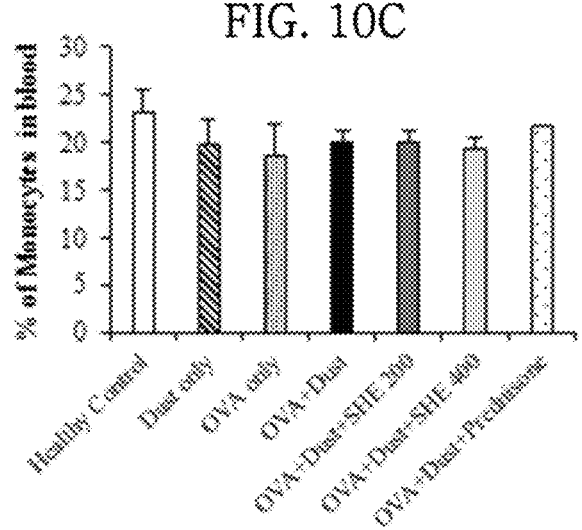
Figure 11A:
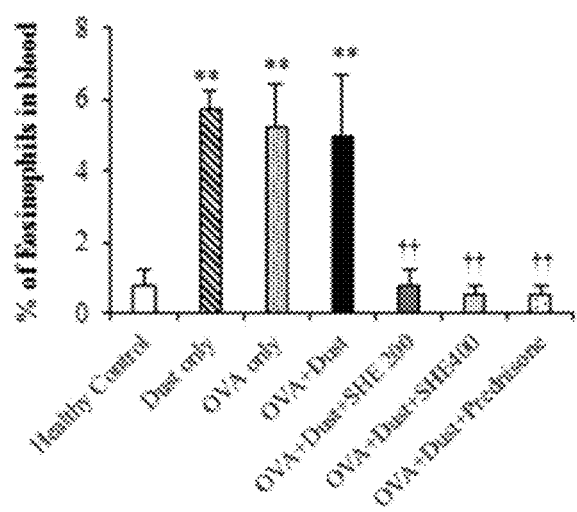
Figure 11B:
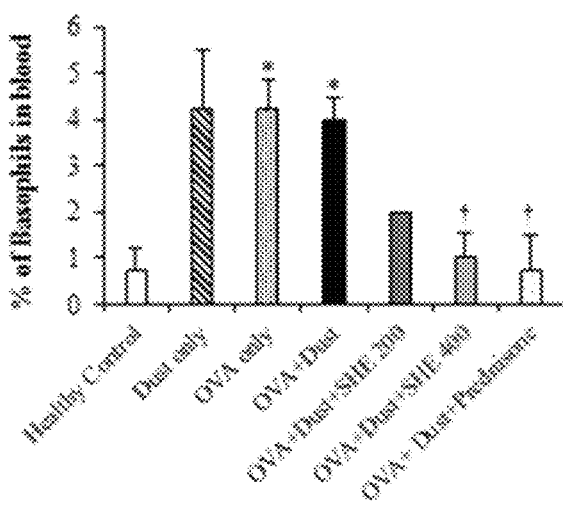

(2) The results of the differential cell counting are shown in FIGS. 10 and 11. The infiltration of neutrophils, eosinophils and basophils significantly increased in the OVA+dust group compared to the healthy control group (FIGS. 10A, 11A and 11B). The infiltration of eosinophils decreased by 6.6-fold in the OVA+dust+200 mg/kg SHE group administered with the SHE, and decreased by 10.0-fold in the OVA+dust+400 mg/kg SHE group (FIG. 11A). In addition, in the OVA+dust+400 mg/kg SHE group, the infiltration of neutrophils decreased by 1.5-fold (FIG. 10A), and the infiltration of basophils decreased by 3.0-fold (FIG. 11B). However, the infiltration of lymphocytes and monocytes was not changed by OVA and particulate matter (FIGS. 10B and 10C).

Experimental Example 8-3: Effect of *Sargassum horneri* Extract (SHE) on Differential Cell Count in Bronchoalveolar Lavage Fluid (BALF) of Particulate Matter-Inhaled Animal Models (1) Since cells contained in bronchoalveolar lavage fluid reflect the inflammatory state of lung tissue and bronchi (J Toxicol Environ Health A 2017, 80(4), 197-207), changes in differential cell counts of bronchoalveolar lavage fluid were observed to evaluate the effect of the *Sargassum horneri* extract (SHE) on pulmonary and bronchial inflammations caused by particulate matter inhalation.

(2) The euthanized, and then bronchoalveolar lavage fluid was collected by injecting DPBS into the airway by an intra-tracheal catheter. The collected bronchoalveolar lavage fluid was centrifuged at 3000 g and 4° C. for 5 minutes, and then fixed with methanol and attached to a slide. The cell-attached slide was stained with Diff-Qick solution, and neutrophils, lymphocytes, monocytes, eosinophils and basophils were counted under a microscope and compared.

Figure 12A:
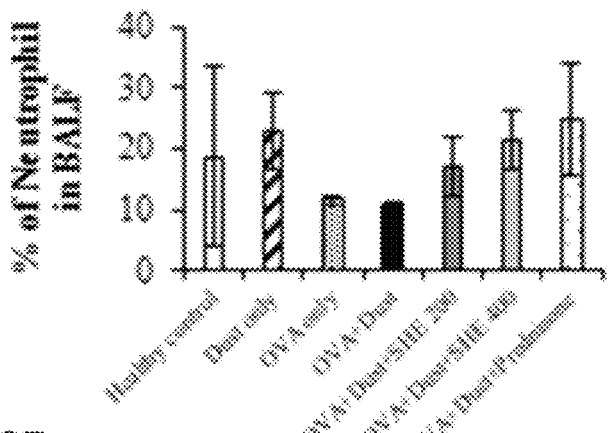
FIGS. 12A, 12B, 12C, 13A and 13B show the results of evaluating the effect of a *Sargassum horneri* extract on differential cell count in the bronchoalveolar lavage fluid (BALF) of particulate matter-inhaled animal models.
Figure 12B:
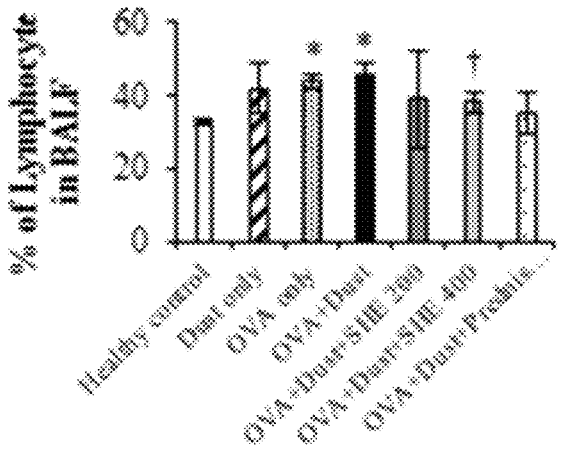
Figure 12C:
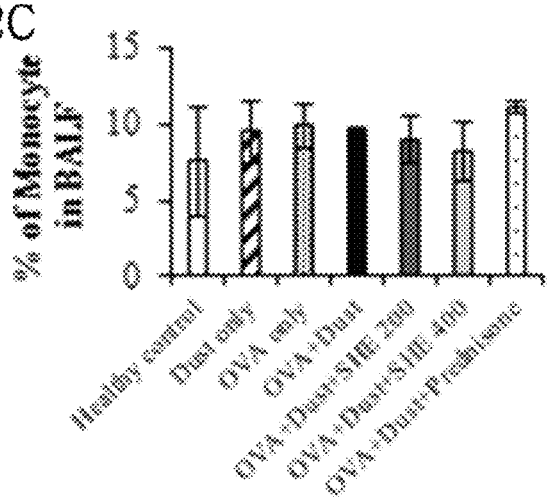
Figure 13A:
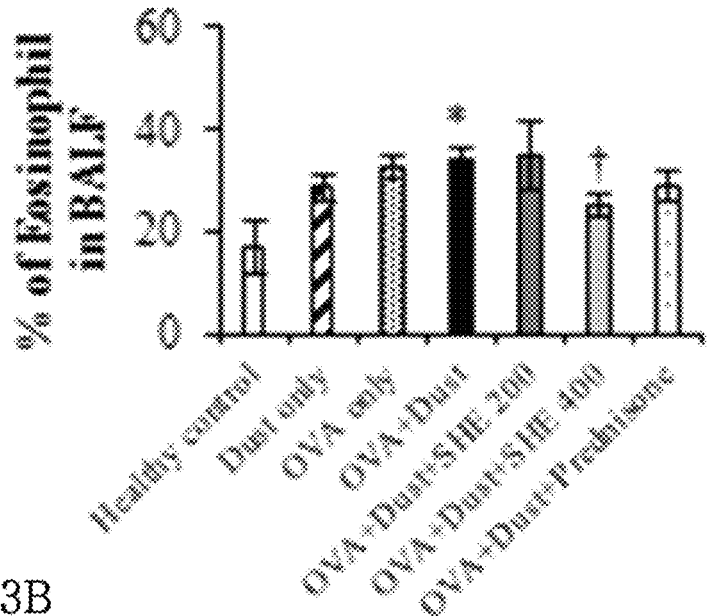
Figure 13B:
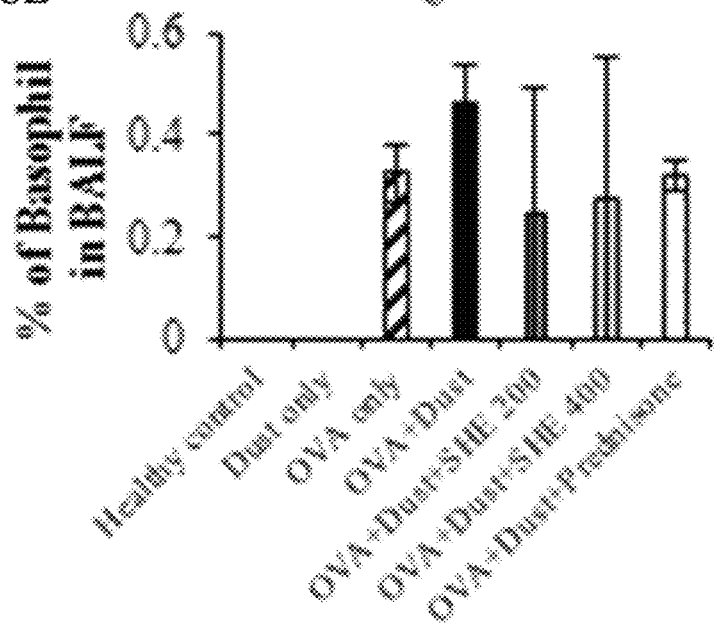

(3) The results of the differential cell counting are shown in FIGS. 12 and 13. The infiltration of lymphocytes and eosinophils significantly increased in the OVA+dust group compared to the healthy control group (FIGS. 12B and 13A). In the OVA+dust+400 mg/kg SHE group administered with the SHE and the allergic respiratory inflammation anti-inflammatory drug-administered group, the infiltration of lymphocytes and eosinophils significantly decreased, and the infiltration of basophils showed a tendency to decrease without significance (FIGS. 12B, 13A and 13B). However, the infiltration of neutrophils and monocytes was not changed by OVA and particulate matter (FIGS. 12A and 12C).

Experimental Example 8-4: Effect of *Sargassum horneri* Extract (SHE) on Histopathological Changes of Tracheas and Lungs of Particulate Matter-Inhaled Animal Models (1) The BALB/c mice were euthanized and autopsied, and the tracheas and lungs were collected, and then paraffin blocks were prepared according to a conventional method. The paraffin blocks were sectioned to 3 μm, attached to slides, deparaffinized, dehydrated, stained with Mayer's hematoxylin solution and eosin solution, dehydrated, cleared, and then mounted.

Figure 14A:
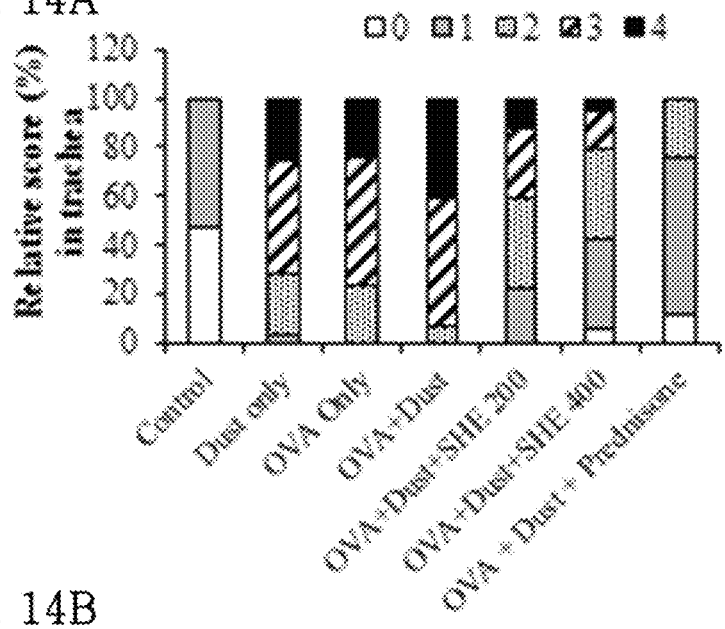
FIGS. 14A and 14B show the results of evaluating the effect of a *Sargassum horneri* extract on the histopathological changes of tracheas and lungs in particulate matter-inhaled animal models. (0, normal; 1, few cells observed; 2, a ring of inflammatory cells one cell layer deep; 3, a ring of inflammatory cells 2-4 cells deep; and 4, a ring of inflammatory cells >4 cells deep).
Figure 14B:
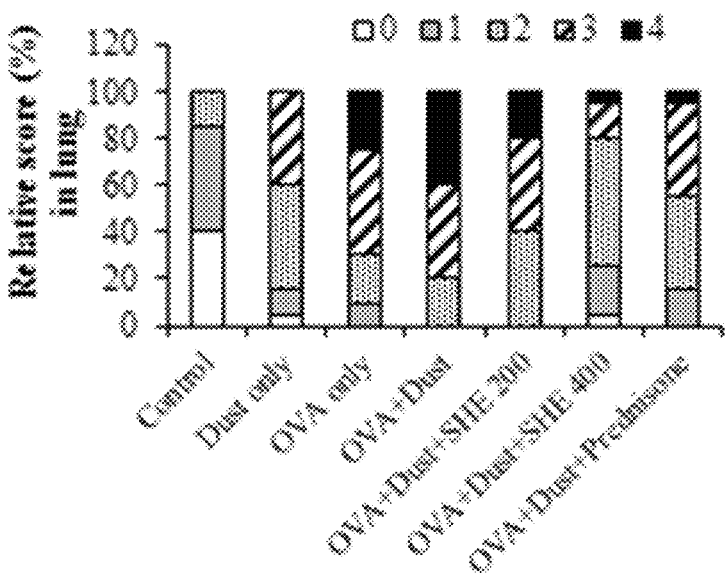

(2) The results are shown in FIG. 14. The infiltration of inflammatory cells significantly increased in the tracheas of the OVA+dust group compared to the healthy control (FIG. 14A), whereas the infiltration of inflammatory cells decreased in the tracheas of the OVA+dust+200 mg/kg SHE administered with the SHE. In particular, it was confirmed that the infiltration of inflammatory cells in the OVA+dust+400 mg/kg SHE group effectively decreased to a level similar to that in the allergic respiratory inflammation anti-inflammatory drug-administered group (FIG. 14A). In the lung tissue, similarly to the trachea, the infiltration of inflammatory cells in the OVA+dust group significantly increased compared to that in the healthy control group (FIG. 14B), whereas the infiltration of inflammatory cells into lung tissue in the OVA+dust+200 mg/kg SHE and 400 mg/kg SHE groups administered with the SHE significantly decreased in a SHE concentration-dependent manner (FIG. 14B). In the graph of FIG. 14, 0, normal; 1, few cells observed; 2, a ring of inflammatory cells one cell layer deep; 3, a ring of inflammatory cells 2-4 cells deep; and 4, a ring of inflammatory cells >4 cells deep.

Experimental Example 8-5: Effect of *Sargassum horneri* Extract (SHE) on Change in 8-OHdG Expression in Lungs of Particulate Matter-Inhaled Animal Models (1) 8-Hydroxy-2'-deoxyguanosine (8-OHdG), a marker of oxidative stress-induced DNA damage, is produced when the hydroxyl group at position 8 of a guanine molecule among DNA bases is oxidized. 8-OHdG is used as a marker for evaluating the degree of DNA damage caused by reactive oxygen species (ROS) that causes oxidative stress (Particle and fibre toxicology, 2017, 14(38)). Thus, the degree of oxidative stress caused by particulate matter inhalation and the antioxidant effect of the *Sargassum horneri* extract (SHE) were evaluated by immunocytochemistry (ICC).

(2) The BALB/c mice were euthanized and autopsied, and the lung tissue was collected, and then prepared into a paraffin block according to a conventional method. The paraffin block was sectioned to 3 μm, and the section was attached to a slide, and then subjected to immunohistochemistry (IHC). To analyze the expression of 8-OHdG, the section was allowed to react with an anti-8-OHdG antibody (1:2000) at room temperature for 1 hour. After completion of the reaction, the section was allowed to react with biotinylated anti-goat IgG at room temperature for 30 minutes and developed with 3,3'-diaminobenzidine (DAB), and positive cells were counterstained with a hematoxylin solution, and then observed with an optical microscope.

Figure 15:
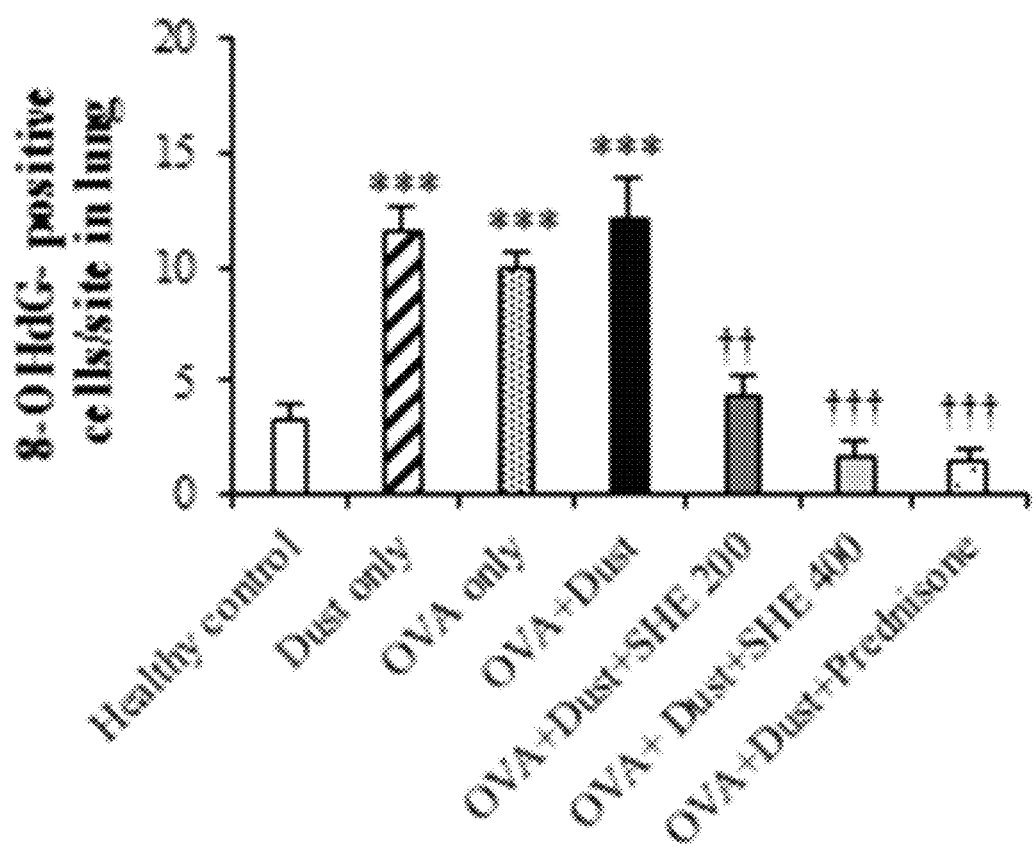
FIG. 15 shows the results of evaluating the effect of a *Sargassum horneri* extract on a change in the expression of 8-OHdG in the lungs of particulate matter-inhaled animal models.

(3) The results of analyzing the expression of 8-OHdG are shown in FIG. 15. In neutrophils, eosinophils and epithelial cell nuclei, 8-OHdG-positive cells significantly increased in the dust only group, the OVA only group and the OVA+dust group compared to the healthy control group, but 8-OHdG-positive cells significantly decreased in the OVA+dust+200 mg/kg SHE group and the OVA+dust+400 mg/kg SHE group. In particular, 8-OHdG-positive cells in the OVA+dust+400 mg/kg SHE group significantly decreased to levels similar to those in the OVA+dust+5 mg/kg Prednisone.

Experimental Example 8-6: Effect of *Sargassum horneri* Extract (SHE) on Changes in Expression of Gr-1 in Tracheas and Lungs of Particulate Matter-Inhaled Animal Models (1) Gr-1, a granulocyte marker involved in the differentiation and maturation of granulocytes, is known to act on immune mechanisms by secreting cytokines when infection or the like occurs (Immunity 2012, 36(3), 451-63). Thus, the effect of the *Sargassum horneri* extract (SHE) on the particulate matter inhalation-induced infiltration of granulocytes into trachea and lung tissue was examined.

(2) The BALB/c mice were euthanized and autopsied, and the trachea and lung tissue were collected, and then prepared into paraffin blocks according to a conventional method. The paraffin tissues were sectioned to 3 μm, attached to slides, deparaffinized, dehydrated, and then immersed in 0.3% hydrogen peroxide solution in order to inhibit endogenous peroxidase in the tissue. Next, in order to nonspecific immune responses, the section was allowed to react with blocking rat serum for 30 minutes, and then allowed to react with mouse Ly-6G/Ly-6C (1:200, R&D Systems) at 4° C. overnight. After completion of the reaction, the section was allowed to react with biotinylated anti-rabbit serum at room temperature for 45 minutes, and then developed with 3,3'-diaminbenzidine (DAB, Vector) and counterstained with a hematoxylin solution. Between the steps, the section was washed sufficiently with phosphate buffered saline (PBS), 0.3% PBS-triton X100, dehydrated, cleared, and then mounted.

Figure 16A:
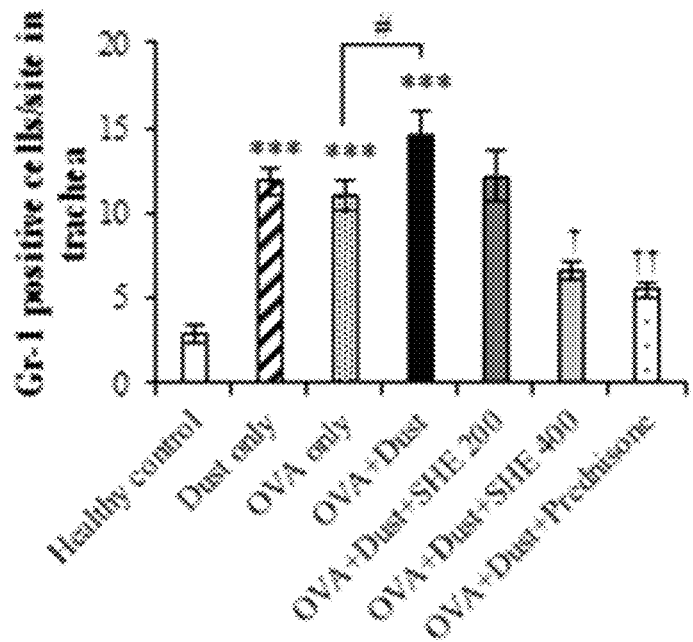
FIGS. 16A and 16B show the results of evaluating the effect of a *Sargassum horneri* extract on a change in the expression of Gr-1 in the tracheas and lungs of particulate matter-inhaled animal models.
Figure 16B:
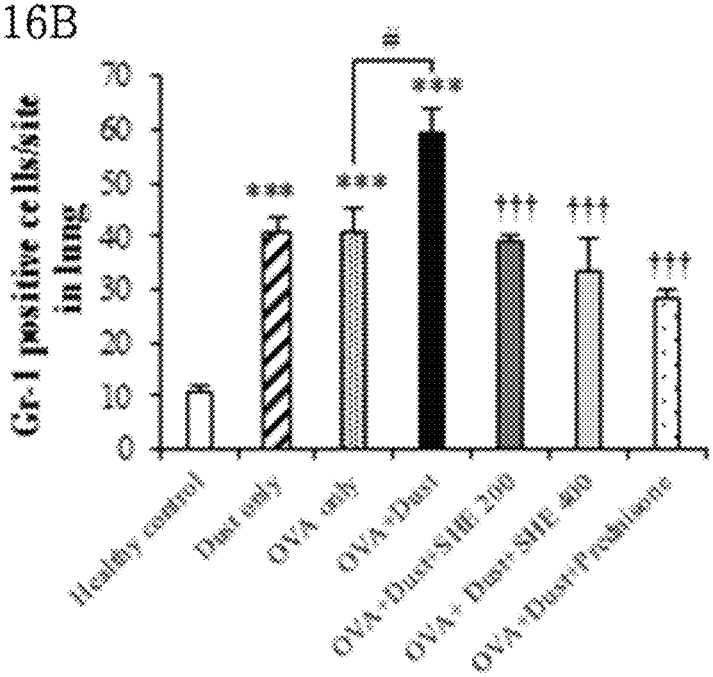

(3) The results are shown in FIG. 16. The granulocyte infiltration of trachea in the OVA+dust group significantly increased by 5.2-fold compared to that in the healthy control, whereas the infiltration of granulocytes in the OVA+dust+200 mg/kg SHE and 400 mg/kg SHE groups administered with the SHE decreased. In particular, the infiltration of granulocytes in the group administered with 400 mg/kg of the SHE significantly decreased by 2.2-fold, which was similar to that in the allergic respiratory inflammation anti-inflammatory drug-administered group (FIG. 16A). In the lung tissue, similarly to the trachea, the infiltration of granulocytes into trachea in the OVA+dust group significantly increased by 5.6-fold compared to that in the healthy control group, whereas the infiltration of granulocytes in the OVA+dust+200 mg/kg SHE and 400 mg/kg SHE groups administered with the SHE significantly decreased by 1.5-fold and 1.7-fold, respectively (FIG. 16B). This decrease in the infiltration of granulocytes was similar to that in the allergic respiratory inflammation anti-inflammatory drug-administered group (2.0-fold decrease in granulocyte infiltration compared to the healthy control group), suggesting that administration of the SHE effectively inhibited the particulate matter-induced infiltration of granulocytes into trachea and lung tissue.

Example 8-7: Effect of *Sargassum horneri* Extract (SHE) on Infiltration of Eosinophilic Leukocytes into Trachea and Lung Tissue in Particulate Matter-Inhaled Animal Models (1) The characteristic pathologic findings of chronic allergic respiratory inflammatory disease are increased eosinophilic leukocytes, and eosinophils containing inflammatory proteins play an important role in the onset of allergic respiratory inflammation by inducing airway epithelial cell damage, increasing airway hypersensitivity, and inducing degranulation of mast cells (World Allergy Organ J 2016, 9, 7). Thus, the effect of the *Sargassum horneri* extract (SHE) on the particulate matter inhalation-induced infiltration of eosinophilic leukocytes into trachea and lung tissue was examined.

(2) The BALB/c mice were euthanized and autopsied, and the trachea and lung tissue were collected, and then prepared into paraffin blocks according to a conventional method. The paraffin blocks were sectioned to 3 μm and attached to slides, and then the tissue section was stained with 0.05% Congo red in 50% EtOH solution and mounted.

Figure 17A:
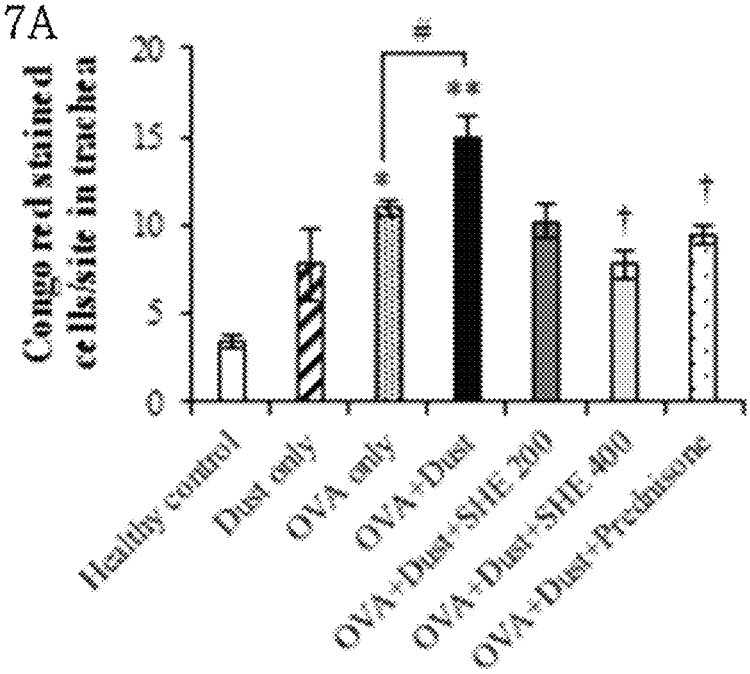
FIGS. 17A and 17B show the results of evaluating the effect of a *Sargassum horneri* extract on the infiltration of eosinophilic leukocytes into trachea and lung tissue in particulate matter-inhaled animal models.
Figure 17B:
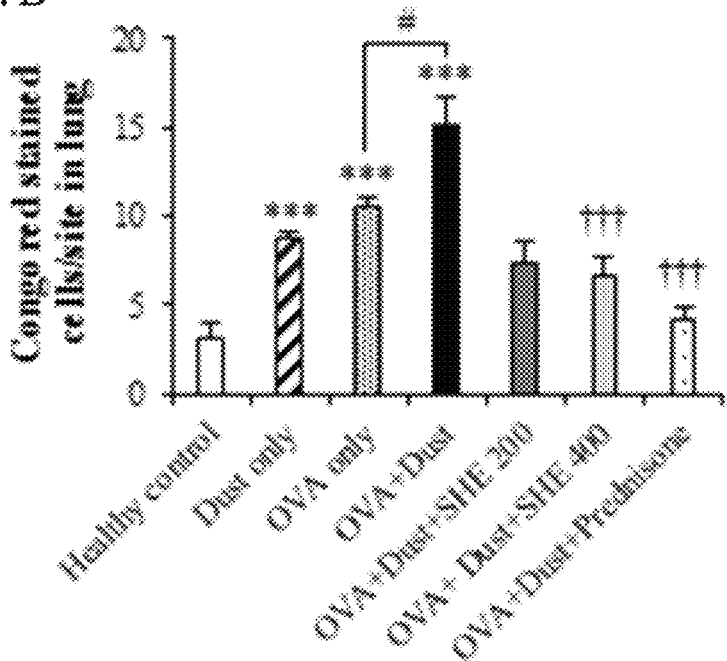

(3) The results are shown in FIG. 17. The infiltration of eosinophilic leukocytes into trachea in the OVA+dust group significantly increased by 4.4-fold compared to that of the healthy control group, whereas the infiltration of eosinophilic leukocytes in the OVA+dust+200 mg/kg SHE and 400 mg/kg SHE groups administered with the SHE showed a tendency to decrease. In particular, the infiltration of eosinophilic leukocytes in the group administered with 400 mg/kg of the SHE significantly decreased by 1.9-fold (FIG. 17A). In the lung tissue, similarly to the trachea, the infiltration of eosinophilic leukocytes in the OVA+dust group significantly increased compared to that in the healthy control group, and the infiltration of eosinophilic leukocytes in the group administered with the SHE showed a tendency to decrease in a concentration-dependent manner. In particular, the infiltration of eosinophils in the OVA+dust+400 mg/kg SHE group decreased by 1.7-fold (FIG. 17B).

Experimental Example 8-8: Effect of *Sargassum horneri* Extract (SHE) on Infiltration of Mast Cells into Trachea in Particulate Matter-Inhaled Animal Models (1) Mast cells are mainly found in connective tissue and mucosa, and are characterized by having granules in the cytoplasm. Granulocytes contain chemical mediators, such as histamine, prostaglandin and cytokines, and are released when mast cells are activated by external stimuli, and thus these granulocytes are involved in inflammatory responses, hypersensitive responses, etc., causing bronchial constriction, increased mucus secretion, etc. (World Allergy Organ J 2016, 9, 7). Thus, the effect of the *Sargassum horneri* extract (SHE) on the particulate matter inhalation-induced infiltration of mast cells into trachea was examined.

(2) The BALB/c mice were euthanized and autopsied, and the trachea was collected, and then prepared into a paraffin block according to a conventional method. The paraffin block was sectioned to 3 μm and attached to a slide, and then the tissue section was stained with 0.05% Toluidine blue solution and mounted.

Figure 18A:
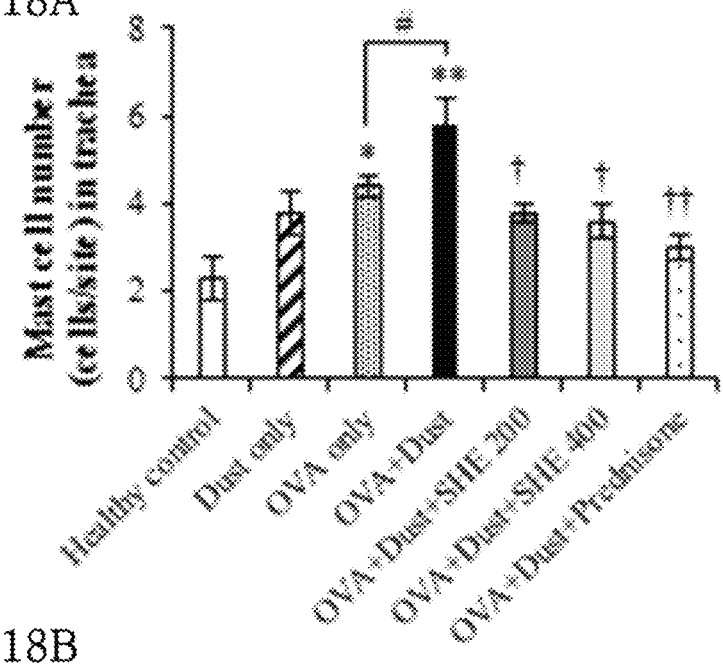
FIGS. 18A and 18B show the results of evaluating the effect of a *Sargassum horneri* extract on the infiltration of mast cells into trachea in particulate matter-inhaled animal models.
Figure 18B:
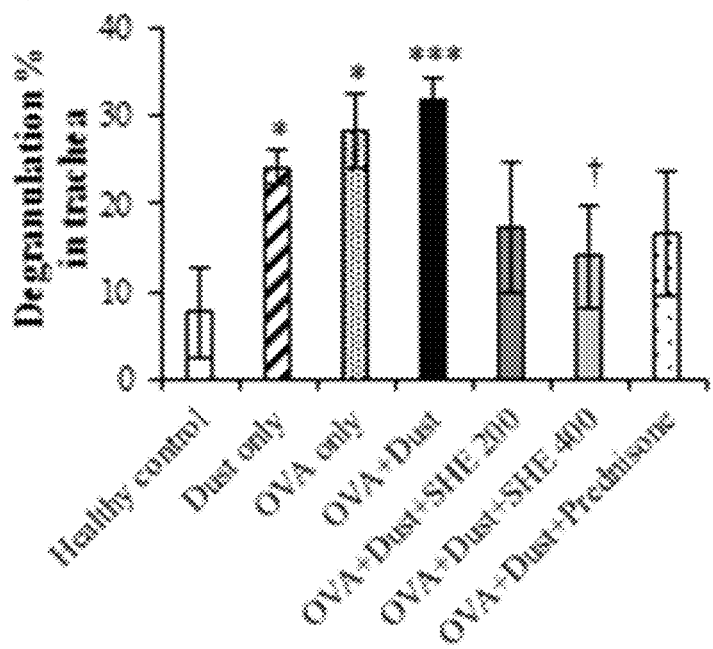

(3) The results are shown in FIG. 18. The infiltration of mast cells into trachea in the OVA+dust group significantly increased compared to the healthy control group, and also significantly increased compared to that in the OVA only group and the dust only group (FIG. 18A). However, the infiltration of mast cells into trachea in the OVA+dust+200 mg/kg SHE and 400 mg/kg SHE groups administered with the SHE significantly decreased (FIG. 18A). In addition, the degranulation rate of mast cells in the OVA+dust group increased compared to that in the healthy control group (FIG. 18B), and significantly increased in the OVA only group and the dust only group (FIG. 18B). However, the degranulation rate of mast cells in the OVA+dust+200 mg/kg SHE and 400 mg/kg SHE groups administered with the SHE decreased, and particularly, the degranulation rate of mast cells in the OVA+dust+400 mg/kg SHE group effectively decreased compared to that in the OVA+dust+5 mg/kg Prednisone group (FIG. 18B).

Experimental Example 8-9: Effect of *Sargassum horneri* Extract (SHE) on Mucus Secretion and Goblet Cell Proliferation in Particulate Matter-Inhaled Animal Models (1) In the case of exposure to repeated airway inflammation due to foreign substances, airway remodeling occurs, and symptoms, such as increased goblet cells and mucous gland hyperplasia, appear (Chest 2018, 154(1), 169-176). Thus, the effect of the *Sargassum horneri* extract (SHE) on the mucus secretion and goblet cell proliferation caused by particulate matter inhalation was examined.

(2) The BALB/c mice were euthanized and autopsied, and the trachea and lung tissue were collected, and then prepared into paraffin blocks according to a conventional method. The paraffin blocks were sectioned to 3 μm, attached to slides, and then stained with periodic acid of Schiff (PAS). In addition, for staining with anti-mucin 5AC antibody (R&D Abcam), the paraffin blocks were sectioned to 3 μm, attached to slides, and then deparaffinized, dehydrated, and immersed in 0.3% hydrogen peroxide solution in order to inhibit endogenous peroxidase in the tissue. Next, in order to inhibit nonspecific reactions, the section was allowed to react with blocking horse serum for 30 minutes, and then allowed to react with anti-mucin 5AC antibody (1:500, R&D Abcam) at 4° C. overnight. After completion of the reaction, the section was allowed to react with biotinylated anti-mouse serum at room temperature for 45 minutes, and then developed with 3, 3'-diaminbenzidine (DAB, Vector) and counterstained with a hematoxylin solution. Between the steps, the section was washed sufficiently with phosphate buffered saline (PBS), 0.3% PBS-triton X100, and dehydrated, cleared, and then mounted.

Figure 19A:
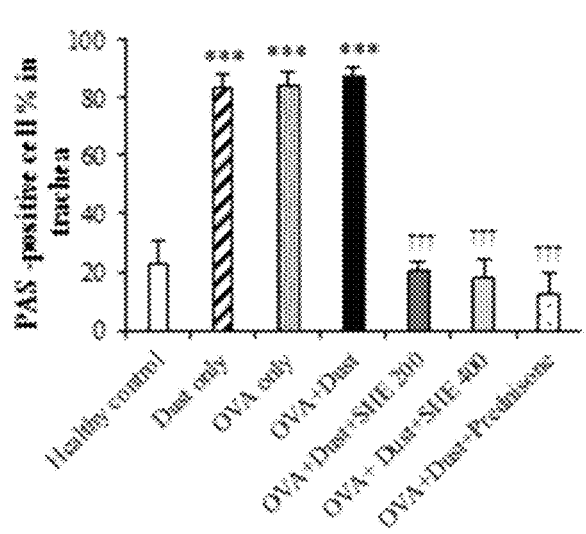
Figure 19B:
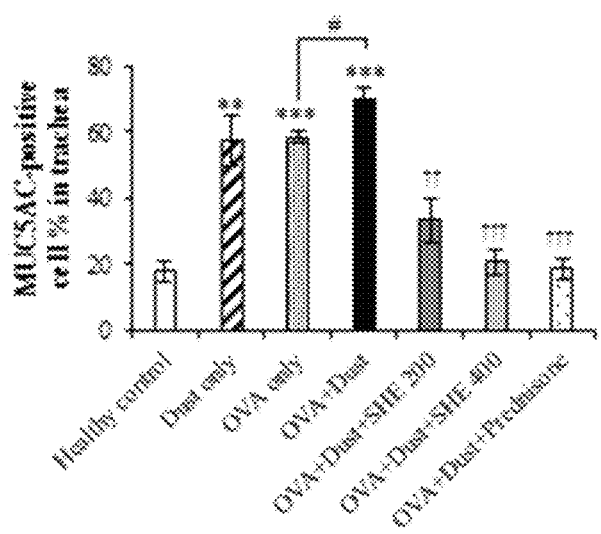
Figure 21A:
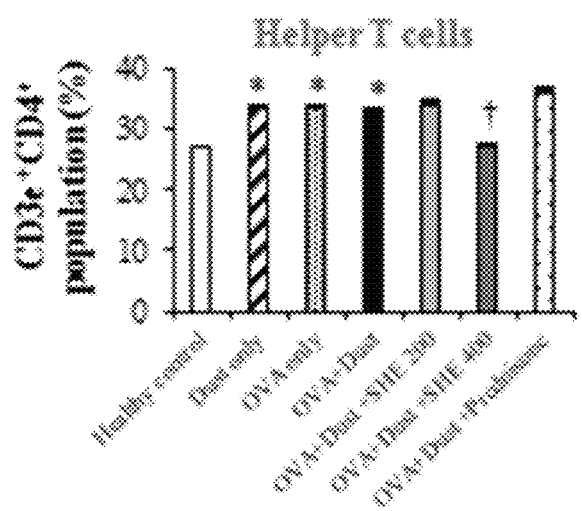
FIGS. 21A, 21B, 21C and 21D show the results of evaluating the effects of a *Sargassum horneri* extract on cell population changes in the lung tissue of particulate matter-inhaled animal models.
Figure 21B:
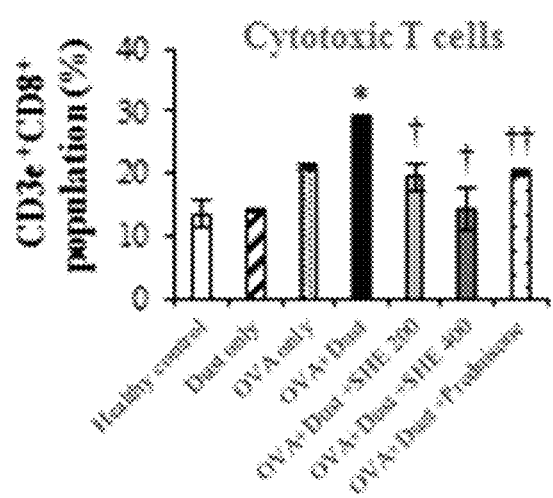
Figure 21C:
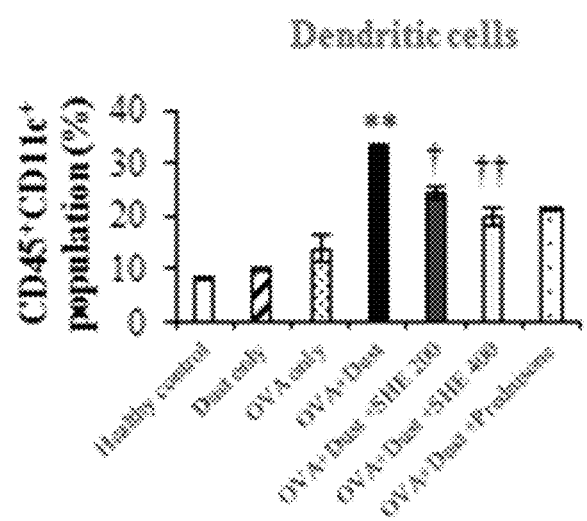
Figure 21D:
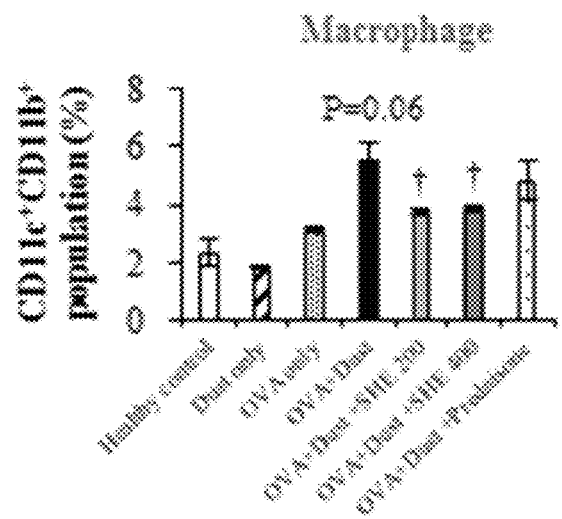

(3) The results are shown in FIGS. 19 and 20. In the results of trachea PAS and immunohistochemical staining for the mucin-5AC antibody, mucus secretion in the OVA+dust group increased compared to that in the healthy control, and excessive goblet cell proliferation was observed in the OVA+dust group. However, in the group administered with the SHE, mucus secretion and goblet cell proliferation decreased. In particular, mucus secretion and goblet cell proliferation in the OVA+dust+400 mg/kg SHE group decreased to levels similar to those in the OVA+dust+5 mg/kg Prednisone group (FIGS. 19A and 19B). Meanwhile, mucus secretion into trachea in the OVA+dust group significantly increased compared to those in the OVA only group and the dust only (FIG. 19B).

(4) In addition, mucus secretion in the lung tissue of the OVA+dust group increased compared to that in the healthy control group, and excessive proliferation of goblet cells was observed in the OVA+dust group. However, mucus secretion and goblet cell proliferation in the OVA+dust+200 mg/kg SHE and 400 mg/kg SHE groups administered with the SHE decreased to levels similar to those in the OVA+dust+5 mg/kg Prednisone group in a concentration-dependent manner (FIGS. 20A and 20B).

Experimental Example 8-10: Effect of *Sargassum horneri* Extract (SHE) on Cell Population Changes in Lung Tissue of Particulate Matter-Inhaled Animal Models (1) Allergic respiratory inflammatory diseases are chronic inflammatory diseases in which the immune system is involved, and are characterized by the infiltration of T cells and eosinophils and the activation of mast cells and basophils (World Allergy Organ J 2016, 9, 7). Thus, in order to evaluate the effect of the *Sargassum horneri* extract (SHE) on particulate matter inhalation-induced changes in immune cell populations, analysis was performed using flow cytometry.

(2) The BALB/c mice were euthanized and autopsied, and the lung was collected, sectioned finely, allowed to react with 0.4 mg/ml of collagenase at 37° C. for 30 minutes, and stirred well at 8-10-minute intervals. Next, PBS was added thereto, and the solution was stirred well at 1500 rpm for 5 minutes. Next, for leukocyte lysis, ACK solution was added, and the mixture was allowed to react at room temperature for 10 minutes, and then washed with DPBS. The pulmonary single cell suspension was treated with an Fc blocker at 4° C. for 15 minutes to reduce nonspecific reactions. Next, the cells were allowed to react with FITC- or PE-, PerCp-CyTM5.5-, BV421-, AF700-labeled CD3e (145-2C11), CD4 (H129.19), CD8a (53-6.7), CD45 (30-F11), CD11b (M1/70), and CD11c (HL3) antibodies at 4° C. for 15 minutes. Next, the cells were washed with PBS and analyzed using the CytoFLEX flow cytometer (Beckman Coulter, Inc., Kraemer Blvd, Calif., USA).

(3) The results are shown in FIG. 21. The number of $CD3e^+CD4^+$ helper T cells in the OVA+dust group increased by 1.3-fold compared to that in the healthy control group, and the number of $CD3e^+CD4^+$ helper T cells in the OVA+dust+400 mg/kg SHE administered with the SHE significantly decreased by 1.2-fold (FIG. 21A). In addition, the number of $CD3e^+CD8^+$ cytotoxic T cells significantly increased in the OVA+dust group compared to the healthy control group, and the numbers of $CD3e^+CD8^+$ cytotoxic T cells in the OVA+dust+200 mg/kg SHE and 400 mg/kg SHE groups administered with the SHE significantly decreased by 1.5-fold and 2.0-fold, respectively, in a concentration-dependent manner (FIG. 21B). The number of $CD45^+$ $CD11c^+$ dendritic cells in the OVA+dust group increased by 4.0-fold compared to that in the healthy control group, and the numbers of $CD45^+CD11c^+$ dendritic cells in the OVA+dust+200 mg/kg SHE and 400 mg/kg SHE groups administered with the SHE significantly decreased by 1.3-fold and 1.4-fold, respectively, in a concentration-dependent manner (FIG. 21C). In addition, the number of $CD11^c+CD11b^+$ macrophages in the OVA+dust group showed a tendency to increase compared to that in the healthy control group, and the number of $CD11c^+CD11b^+$ macrophages significantly decreased in the OVA+dust+200 mg/kg SHE and 400 mg/kg SHE groups administered with the SHE (FIG. 21D).

Statistical Processing

Each experiment was repeated 3 times or more (n=3 or more per group). The experimental results were expressed as mean±standard deviation, and significance was analyzed using Student's t-test (Microsoft Office Excel) (\*\*; $P<0.005$, \*\*\*; $P<0.0005$, ††; $P<0.005$, †††; $P<0.0005$, #; $P<0.05$).

As described above, according to the present disclosure, there may be provided a composition for alleviating lung injury caused by particulate matter or the like and a composition for alleviating respiratory disease, in which the composition contains a *Sargassum horneri* extract. The composition of the present disclosure may be commercialized as a functional health food or a pharmaceutical product.

What is claimed is:

1. A tablet or capsule for treating lung injury in a human in need thereof consisting essentially of therapeutically effective amounts of a *Sargassum horneri* extract, honey and bamboo shoots.

2. The tablet or capsule of claim 1, wherein the lung injury is lung injury caused by particulate matter.

3. The tablet or capsule of claim 1, wherein the *Sargassum horneri* extract is an extract obtained by extraction with water, a lower alcohol having 1 to 4 carbon atoms, and a mixed solvent thereof.

4. The tablet or capsule of claim 1, wherein the therapeutically effective amount of a *Sargassum horneri* extract improves lung function in the human in need thereof.

5. The tablet or capsule of claim 1, wherein the therapeutically effective amount is also for alleviating a respiratory disease in said human.

6. The tablet or capsule of claim 5, wherein the respiratory disease is respiratory disease caused by particulate matter.

7. The tablet or capsule of claim 5, wherein the respiratory disease is asthma, chronic obstructive pulmonary disease, tracheitis, bronchitis, or rhinitis.

8. The tablet or capsule of claim 5, wherein the respiratory disease is chronic obstructive pulmonary disease.

* * * * *